US008496606B2

(12) United States Patent
Leonard et al.

(10) Patent No.: US 8,496,606 B2
(45) Date of Patent: Jul. 30, 2013

(54) FLUID SEPARATION DEVICES, SYSTEMS AND METHODS

(75) Inventors: Edward F. Leonard, Bronxville, NY (US); Ilan K. Reich, New York, NY (US); Stanley Cortell, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 233 days.

(21) Appl. No.: 12/866,017

(22) PCT Filed: Feb. 4, 2009

(86) PCT No.: PCT/US2009/033111
§ 371 (c)(1),
(2), (4) Date: Nov. 24, 2010

(87) PCT Pub. No.: WO2009/100154
PCT Pub. Date: Aug. 13, 2009

(65) Prior Publication Data
US 2011/0105982 A1    May 5, 2011

Related U.S. Application Data

(60) Provisional application No. 61/006,866, filed on Feb. 4, 2008, provisional application No. 61/073,951, filed on Jun. 19, 2008.

(51) Int. Cl.
*A61M 1/14* (2006.01)
*A61M 1/16* (2006.01)
*A61M 1/34* (2006.01)
*A61M 1/36* (2006.01)
*B01D 61/24* (2006.01)
*B01D 61/58* (2006.01)

(52) U.S. Cl.
USPC ....... 604/6.01; 604/4.01; 604/5.01; 604/5.04; 604/6.04; 604/6.09; 604/6.11

(58) Field of Classification Search
USPC ................... 604/4.01, 5.01, 5.04, 6.01, 6.04, 604/6.09, 6.11
See application file for complete search history.

(56) References Cited

U.S. PATENT DOCUMENTS 2,885,782 A    5/1959    Groves
3,388,803 A    6/1968    Scott
(Continued)

FOREIGN PATENT DOCUMENTS

DE    20113789    5/2002
EP    1622691    2/2006
(Continued)

OTHER PUBLICATIONS

V Gura, C Ronco, F Nalesso, A Brendolan, M Beizai, C Ezon, A Davenport and E Rambod. "A wearable hemofilter for continuous ambulatory ultrafiltration" Kidney International (2008) 73, 497-502; doi:10.1038/sj.ki.5002711; published online Dec. 5, 2007.*

(Continued)

*Primary Examiner* — Adam Marcetich
(74) *Attorney, Agent, or Firm* — Miles & Stockbridge P.C.; Mark A. Catan

(57) ABSTRACT

A membraneless separation device can be applied to a variety of treatments, such as the ultrafiltration of blood for a patient with end stage renal disease. An ultrafiltration device can include a membraneless separation device, which separates an incoming blood flow into a substantially cytoplasmic body-free plasma flow and remaining fraction, and a dialysate-free second stage, which selectively removes excess fluid, toxins and other substances from the plasma flow and returns the processed plasma to the membraneless separation device. A treatment protocol can include ultrafiltering blood of a patient using the ultrafiltration device and performing a secondary treatment on the blood of the patient at a reduced frequency compared to the ultrafiltering. The membraneless separation device can also be applied to treatment, analysis, and/or exchange of plasma from blood, or combined with conventional dialyzers to perform dialysis on a cytoplasmic body-free plasma fraction.

14 Claims, 9 Drawing Sheets

U.S. PATENT DOCUMENTS

| | | |
|---|---|---|
| 3,506,126 A | 4/1970 | Lindsay et al. |
| 3,619,423 A | 11/1971 | Galletti et al. |
| 3,746,175 A | 7/1973 | Markley |
| 3,799,873 A | 3/1974 | Brown |
| 3,884,808 A | 5/1975 | Scott |
| 3,939,069 A | 2/1976 | Granger et al. |
| 3,989,622 A | 11/1976 | Marantz et al. |
| 3,994,799 A | 11/1976 | Yao et al. |
| 4,066,549 A | 1/1978 | Oeser et al. |
| 4,083,786 A | 4/1978 | Tsuda et al. |
| 4,094,775 A | 6/1978 | Mueller |
| 4,137,921 A | 2/1979 | Okuzumi et al. |
| 4,153,554 A | 5/1979 | von der Heide et al. |
| 4,166,800 A | 9/1979 | Fong |
| 4,181,983 A | 1/1980 | Kulkarni |
| 4,212,738 A | 7/1980 | Henne |
| 4,212,742 A | 7/1980 | Solomon et al. |
| 4,243,775 A | 1/1981 | Rosensaft et al. |
| 4,247,393 A | 1/1981 | Wallace |
| 4,267,040 A | 5/1981 | Schal |
| 4,269,708 A | 5/1981 | Bonomini et al. |
| 4,279,249 A | 7/1981 | Vert et al. |
| 4,300,565 A | 11/1981 | Rosensaft et al. |
| 4,321,192 A | 3/1982 | Jain |
| 4,347,234 A | 8/1982 | Wahlig et al. |
| 4,384,975 A | 5/1983 | Fong |
| 4,390,519 A | 6/1983 | Sawyer |
| 4,394,370 A | 7/1983 | Jefferies |
| 4,409,332 A | 10/1983 | Jefferies et al. |
| 4,431,019 A | 2/1984 | Kopp et al. |
| 4,443,333 A | 4/1984 | Mahurkar |
| 4,530,449 A | 7/1985 | Nozawa et al. |
| 4,538,603 A | 9/1985 | Pawelchak et al. |
| 4,539,981 A | 9/1985 | Tunc |
| 4,563,489 A | 1/1986 | Urist |
| 4,568,559 A | 2/1986 | Nuwayser et al. |
| 4,578,384 A | 3/1986 | Hollinger |
| 4,585,797 A | 4/1986 | Cioca |
| 4,596,574 A | 6/1986 | Urist |
| 4,623,588 A | 11/1986 | Nuwayser et al. |
| 4,661,246 A | 4/1987 | Ash |
| 4,663,049 A | 5/1987 | Kolff et al. |
| 4,678,566 A | 7/1987 | Watanabe et al. |
| 4,703,108 A | 10/1987 | Silver et al. |
| 4,741,337 A | 5/1988 | Smith et al. |
| 4,744,365 A | 5/1988 | Kaplan et al. |
| 4,765,899 A | 8/1988 | Wells et al. |
| 4,765,907 A | 8/1988 | Scott |
| 4,795,804 A | 1/1989 | Urist |
| 4,818,542 A | 4/1989 | DeLuca et al. |
| 4,822,278 A | 4/1989 | Oliva et al. |
| 4,837,285 A | 6/1989 | Berg et al. |
| 4,839,130 A | 6/1989 | Kaplan et al. |
| 4,844,854 A | 7/1989 | Kaplan et al. |
| 4,849,340 A | 7/1989 | Oberhardt |
| 4,877,864 A | 10/1989 | Wang et al. |
| 4,889,119 A | 12/1989 | Jamiolkowski et al. |
| 4,897,189 A | 1/1990 | Greenwood et al. |
| 4,898,186 A | 2/1990 | Ikada et al. |
| 4,898,734 A | 2/1990 | Mathiowitz et al. |
| 4,916,193 A | 4/1990 | Tang et al. |
| 4,938,763 A | 7/1990 | Dunn et al. |
| 4,961,707 A | 10/1990 | Magnusson et al. |
| 4,968,422 A | 11/1990 | Runge et al. |
| 4,968,590 A | 11/1990 | Kuberasampath et al. |
| 4,975,527 A | 12/1990 | Koezuka et al. |
| 4,997,570 A | 3/1991 | Polaschegg |
| 5,004,602 A | 4/1991 | Hutchinson |
| 5,007,939 A | 4/1991 | Delcommune et al. |
| 5,011,691 A | 4/1991 | Oppermann et al. |
| 5,011,692 A | 4/1991 | Fujioka et al. |
| 5,013,649 A | 5/1991 | Wang et al. |
| 5,037,639 A | 8/1991 | Tung |
| 5,051,272 A | 9/1991 | Hermes et al. |
| 5,077,049 A | 12/1991 | Dunn et al. |
| 5,080,665 A | 1/1992 | Jarrett et al. |
| 5,081,106 A | 1/1992 | Bentley et al. |
| 5,084,051 A | 1/1992 | Tormala et al. |
| 5,106,748 A | 4/1992 | Wozney et al. |
| 5,108,753 A | 4/1992 | Kuberasampath et al. |
| 5,108,755 A | 4/1992 | Daniels et al. |
| 5,114,932 A | 5/1992 | Runge |
| 5,116,738 A | 5/1992 | Wang et al. |
| 5,128,136 A | 7/1992 | Bentley et al. |
| 5,133,755 A | 7/1992 | Brekke |
| 5,141,905 A | 8/1992 | Rosen et al. |
| 5,143,730 A | 9/1992 | Fues et al. |
| 5,149,691 A | 9/1992 | Rutherford |
| 5,162,430 A | 11/1992 | Rhee et al. |
| 5,166,058 A | 11/1992 | Wang et al. |
| 5,171,217 A | 12/1992 | March et al. |
| 5,185,152 A | 2/1993 | Peyman |
| 5,187,076 A | 2/1993 | Wozney et al. |
| 5,192,741 A | 3/1993 | Orsolini et al. |
| 5,193,688 A | 3/1993 | Giddings |
| 5,197,977 A | 3/1993 | Hoffman, Jr. et al. |
| 5,206,028 A | 4/1993 | Li |
| 5,227,157 A | 7/1993 | McGinity et al. |
| 5,231,169 A | 7/1993 | Constantz et al. |
| 5,250,584 A | 10/1993 | Ikada et al. |
| 5,268,167 A | 12/1993 | Tung |
| 5,268,178 A | 12/1993 | Calhoun et al. |
| 5,271,961 A | 12/1993 | Mathiowitz et al. |
| 5,278,201 A | 1/1994 | Dunn et al. |
| 5,278,202 A | 1/1994 | Dunn et al. |
| 5,281,419 A | 1/1994 | Tuan et al. |
| 5,284,470 A | 2/1994 | Beltz |
| 5,284,559 A | 2/1994 | Lim et al. |
| 5,288,496 A | 2/1994 | Lewis |
| 5,308,623 A | 5/1994 | Fues et al. |
| 5,320,624 A | 6/1994 | Kaplan et al. |
| 5,324,307 A | 6/1994 | Jarrett et al. |
| 5,324,520 A | 6/1994 | Dunn et al. |
| 5,350,580 A | 9/1994 | Muchow et al. |
| 5,360,610 A | 11/1994 | Tice et al. |
| 5,366,508 A | 11/1994 | Brekke |
| 5,366,733 A | 11/1994 | Brizzolara et al. |
| 5,366,734 A | 11/1994 | Hutchinson |
| 5,376,636 A | 12/1994 | Rutherford et al. |
| 5,415,532 A | 5/1995 | Loughnane et al. |
| 5,437,857 A | 8/1995 | Tung |
| 5,460,803 A | 10/1995 | Tung |
| 5,534,244 A | 7/1996 | Tung |
| 5,562,895 A | 10/1996 | Tung |
| 5,577,891 A | 11/1996 | Lougnane et al. |
| 5,656,153 A | 8/1997 | Kameno et al. |
| 5,716,852 A | 2/1998 | Yager et al. |
| 5,725,776 A | 3/1998 | Kenley et al. |
| 5,744,042 A | 4/1998 | Stange et al. |
| 5,753,014 A | 5/1998 | Van Rijn |
| 5,798,042 A | 8/1998 | Chu et al. |
| 5,833,954 A | 11/1998 | Chow et al. |
| 5,855,562 A | 1/1999 | Moore et al. |
| 5,871,360 A | 2/1999 | Kato |
| 5,885,829 A | 3/1999 | Mooney et al. |
| 5,902,336 A | 5/1999 | Mishkin |
| 5,917,322 A | 6/1999 | Gershenfeld et al. |
| 5,932,100 A | 8/1999 | Yager et al. |
| 5,944,684 A | 8/1999 | Roberts et al. |
| 5,948,684 A | 9/1999 | Weigl et al. |
| 5,980,481 A | 11/1999 | Gorsuch |
| 5,984,891 A | 11/1999 | Keilman et al. |
| 5,993,786 A | 11/1999 | Chow et al. |
| 6,000,341 A | 12/1999 | Tung |
| 6,001,897 A | 12/1999 | Dickens |
| 6,056,930 A | 5/2000 | Tung |
| 6,114,408 A | 9/2000 | Dickens |
| 6,117,100 A | 9/2000 | Powers et al. |
| 6,117,122 A | 9/2000 | Din et al. |
| 6,128,764 A | 10/2000 | Gottesman |
| 6,159,739 A | 12/2000 | Weigl et al. |
| 6,187,838 B1 | 2/2001 | Dickens |
| 6,196,992 B1 | 3/2001 | Keilman et al. |
| 6,197,494 B1 | 3/2001 | Oberhardt |
| 6,206,959 B1 | 3/2001 | Dickens |
| 6,210,759 B1 | 4/2001 | Dickens |
| 6,281,256 B1 | 8/2001 | Harris et al. |

| | | |
|---|---|---|
| 6,317,766 B1 | 11/2001 | Grover |
| 6,332,985 B1 | 12/2001 | Sherman et al. |
| 6,398,859 B1 | 6/2002 | Dickens et al. |
| 6,406,631 B1 | 6/2002 | Collins et al. |
| 6,413,498 B1 | 7/2002 | Malmagro |
| 6,432,630 B1 | 8/2002 | Blankenstein |
| 6,459,097 B1 | 10/2002 | Zagoskin |
| 6,472,210 B1 | 10/2002 | Holy et al. |
| 6,488,896 B2 | 12/2002 | Weigl et al. |
| 6,504,172 B2 | 1/2003 | Zagoskin et al. |
| 6,511,814 B1 | 1/2003 | Carpenter |
| 6,527,735 B1 | 3/2003 | Davankov et al. |
| 6,551,842 B1 | 4/2003 | Carpenter |
| 6,561,997 B1 | 5/2003 | Weitzel et al. |
| 6,563,311 B2 | 5/2003 | Zagoskin |
| 6,582,385 B2 | 6/2003 | Burbank et al. |
| 6,585,682 B1 | 7/2003 | Haraldsson et al. |
| 6,602,719 B1 | 8/2003 | Carpenter |
| 6,605,822 B1 | 8/2003 | Blais et al. |
| 6,614,047 B2 | 9/2003 | Tzalenchuk et al. |
| 6,670,630 B2 | 12/2003 | Blais et al. |
| 6,742,661 B1 | 6/2004 | Schulte et al. |
| 6,743,626 B2 | 6/2004 | Baum et al. |
| 6,758,975 B2 | 7/2004 | Peabody et al. |
| 6,784,451 B2 | 8/2004 | Amin et al. |
| 6,793,725 B2 | 9/2004 | Chow et al. |
| 6,796,955 B2 | 9/2004 | O'Mahoney et al. |
| 6,803,599 B2 | 10/2004 | Amin et al. |
| 6,897,468 B2 | 5/2005 | Blais et al. |
| 6,899,915 B2 | 5/2005 | Yelick et al. |
| 6,900,456 B2 | 5/2005 | Blais et al. |
| 6,911,664 B2 | 6/2005 | Il'ichev et al. |
| 6,930,320 B2 | 8/2005 | Blais et al. |
| 7,002,174 B2 | 2/2006 | Il'ichev et al. |
| 7,052,907 B2 | 5/2006 | Shi et al. |
| 7,118,676 B2 | 10/2006 | Mueth et al. |
| 7,150,834 B2 | 12/2006 | Mueth et al. |
| 7,309,232 B2 | 12/2007 | Rutherford et al. |
| 7,309,323 B2 | 12/2007 | Gura et al. |
| 7,351,218 B2 | 4/2008 | Bene |
| 7,588,550 B2 | 9/2009 | Leonard et al. |
| 7,641,871 B2 | 1/2010 | Futami et al. |
| 7,727,399 B2 | 6/2010 | Leonard et al. |
| 7,850,633 B2 | 12/2010 | Leonard et al. |
| 8,021,318 B2 | 9/2011 | Leonard et al. |
| 8,083,706 B2 | 12/2011 | Leonard et al. |
| 8,092,684 B2 | 1/2012 | Leonard et al. |
| 8,097,153 B2 | 1/2012 | Leonard et al. |
| 8,097,162 B2 | 1/2012 | Leonard et al. |
| 2001/0048637 A1 | 12/2001 | Weigl et al. |
| 2001/0055546 A1 | 12/2001 | Weigl et al. |
| 2002/0052571 A1 | 5/2002 | Fazio |
| 2002/0090644 A1 | 7/2002 | Weigl et al. |
| 2002/0159920 A1 | 10/2002 | Weigl |
| 2002/0172622 A1 | 11/2002 | Weigl et al. |
| 2003/0034306 A1 | 2/2003 | Schulte et al. |
| 2003/0226806 A1 | 12/2003 | Young et al. |
| 2004/0009096 A1 | 1/2004 | Wellman |
| 2004/0016918 A1 | 1/2004 | Amin et al. |
| 2004/0045891 A1 | 3/2004 | Gilbert et al. |
| 2004/0069708 A1 | 4/2004 | Laurell et al. |
| 2004/0082903 A1 | 4/2004 | Micheli |
| 2004/0225249 A1 | 11/2004 | Leonard et al. |
| 2004/0245102 A1 | 12/2004 | Gilbert et al. |
| 2005/0082210 A1 | 4/2005 | Favre |
| 2005/0101901 A1 | 5/2005 | Gura |
| 2005/0121604 A1 | 6/2005 | Mueth et al. |
| 2005/0145497 A1* | 7/2005 | Gilbert et al. ............ 204/600 |
| 2005/0178727 A1 | 8/2005 | Takagi et al. |
| 2005/0201903 A1 | 9/2005 | Weigl et al. |
| 2005/0202563 A1 | 9/2005 | Dasgupta et al. |
| 2005/0215936 A1 | 9/2005 | Gorsuch et al. |
| 2005/0247564 A1 | 11/2005 | Volkel et al. |
| 2005/0266582 A1 | 12/2005 | Modlin et al. |
| 2006/0076295 A1 | 4/2006 | Leonard et al. |
| 2007/0026381 A1 | 2/2007 | Huang et al. |
| 2007/0029257 A1 | 2/2007 | Mueth et al. |
| 2007/0054293 A1 | 3/2007 | Liu et al. |
| 2007/0179435 A1 | 8/2007 | Braig et al. |
| 2007/0179436 A1 | 8/2007 | Braig et al. |
| 2008/0009780 A1 | 1/2008 | Leonard et al. |
| 2008/0015487 A1 | 1/2008 | Szamosfalvi et al. |
| 2008/0023399 A1 | 1/2008 | Inglis et al. |
| 2008/0093298 A1 | 4/2008 | Browning et al. |
| 2009/0139931 A1 | 6/2009 | Leonard et al. |
| 2009/0292234 A1 | 11/2009 | Leonard et al. |
| 2010/0004578 A1 | 1/2010 | Leonard et al. |
| 2010/0198131 A1 | 8/2010 | Leonard et al. |
| 2011/0056884 A1 | 3/2011 | Leonard et al. |
| 2011/0062083 A1 | 3/2011 | Leonard et al. |
| 2011/0066097 A1 | 3/2011 | Leonard et al. |

FOREIGN PATENT DOCUMENTS

| | | |
|---|---|---|
| JP | 10-507962 | 8/1998 |
| JP | 2000-512541 | 9/2000 |
| JP | 2001-511520 | 8/2001 |
| JP | 2002-509248 | 3/2002 |
| JP | 2005-103541 | 4/2005 |
| JP | 2006-520246 | 9/2006 |
| JP | 11-508182 | 7/2009 |
| WO | WO 02/36246 | 5/2002 |
| WO | WO 02/45813 | 6/2002 |
| WO | WO 02/062454 | 8/2002 |
| WO | 2004/082796 | 9/2004 |
| WO | 2006/124431 | 11/2006 |
| WO | WO 2007/137245 | 11/2007 |

OTHER PUBLICATIONS

Abbitt et al., "Rheological Properties of the Blood Influencing Selectin-Mediated Adhesion of Flowing Leukocytes." American Journal of Physiology: Heart and Circulatory Physiology, Jul. 2003, 285(1): pp. H229-H240.

Blackshear, P.L., "Two new concepts that might lead to a wearable artificial kidney," Kidney International, Supplement, Jun. 1978, 8:S133-S137.

Giddings, J.C., "Continuous Separation in Split-Flow Thin (Splitt) Cells Potential Applications To Biological Materials." Separation Science And Technology, 1988, 23(8& 9) : pp. 931-943.

Goldsmith et al., "Margination of Leukocytes in Blood Flow Through Small Tubes" Microvascular Research, Mar. 1984, 27(2): pp. 204-222.

Harper, G., "Home Hemodialysis: A Patient's Perspective." Home Hemodialysis International, 1997, 1: pp. 8-11.

Henne et al, "A Wearable Artificial-Kidney," Artificial Organs, 1977, 1(1): p. 126.

Leonard et al., "Dialysis without Membranes: How and Why?," Blood Purification, 2004, 22 (1):pp. 92-100.

Leonard et al., "Membraneless Dialysis—Is it Possible?" Contributions to Nephrology, 2005, 149: pp. 343-353.

Levin et al., "Analytical Splitt Fractionation In The Diffusion Mode Operating as a Dialysis-Like System Devoid of Membrane—Application To Drug-Carrying Liposomes." Analytical Chemistry, 1993, 65(17): pp. 2254-2261.

Neff et al., "A Wearable Artificial Glomerulus," Transactions—American Society for Artificial Internal Organs, 1979, 25: pp. 71-73.

Ronco, C., "Microfluidic, Membrane-Free Dialysis," American Society of Nephrology, Annual Meeting. 2002.

Schmuhl et al., "Si-Supported Mesoporous and Microporous Oxide Interconnects as Electrophoretic Gates for Application in Microfuidic Devices." Analytical Chemistry, Jan. 2005, 77(1): pp. 178-184.

Seo et al., "Improvement Of The Wearable Artificial Kidney," International Journal of Artificial Organs, 1981, 5(3): pp. 321.

Singh et al., "Haematocrit Dependence Of Cellular Axial Migration And Tubular Pinch Effects In Blood Flow Through Glass Capillaries," Current Science, Feb. 1990, 59(4): pp. 223-226.

Takai et al., "A New Treatment Strategy Using Both Intermittent Short Dialysis and Continuous Ambulatory Hemofiltration," Transactions of the American Society for Artificial Internal Organs, 1991, 37(3):pp. M325-M327.

Takayama et al., "Topographical Micropatterning of Poly(dimethylsiloxane) Using Laminar Flows of Liquids in Capillaries," Advanced Materials, Apr. 2001, 13(8): pp. 570-574.

Vanholder et al., "Pitfalls Of Wearable Artificial-Kidney," International Journal Of Artificial Organs, 1990, 13(11): pp. 715-719.
Extended European Search Report and Search Opinion issued Apr. 13, 2011, in European Patent Application No. 09707117.

Communication Pursuant to Art. 94(3) EPC issued Feb. 2, 2012, in European Patent Application No. 09707117.

* cited by examiner

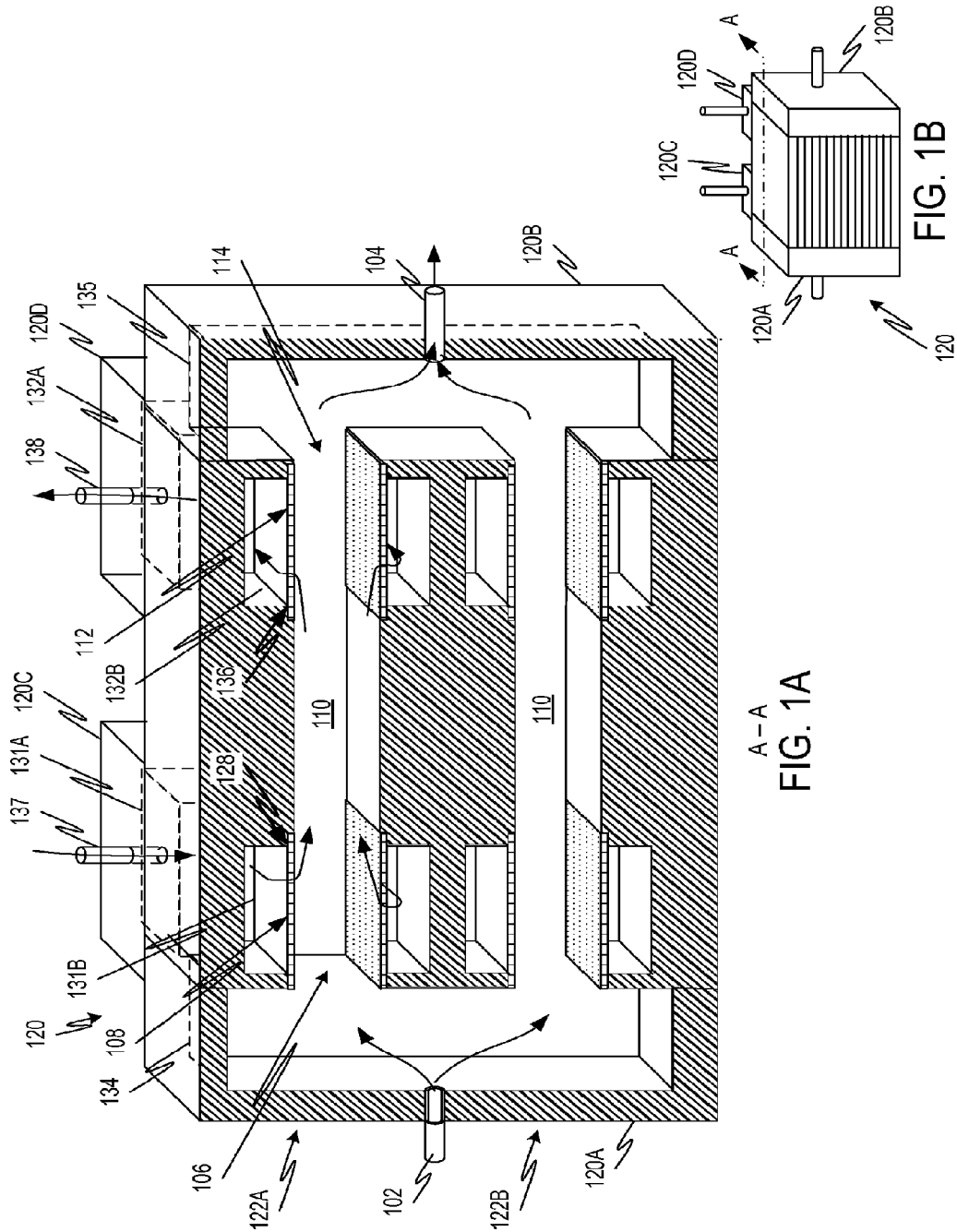

A – A

US 8,496,606 B2

FLUID SEPARATION DEVICES, SYSTEMS AND METHODS

CROSS-REFERENCE TO RELATED APPLICATIONS

The present application is a national stage application of International Application No. PCT/US09/33111, filed Feb. 4, 2009, which claims the benefit of U.S. Provisional Application No. 61/006,866, filed Feb. 4, 2008, expired, and U.S. Provisional Application No. 61/073,951, filed Jun. 19, 2008, expired, the disclosures of all of which are hereby incorporated by reference herein in their entireties.

STATEMENT REGARDING FEDERALLY SPONSORED RESEARCH

This invention was made with government support under HL088162 awarded by the National Institutes of Health (NIH). The government has certain rights in the invention.

FIELD

The present disclosure relates generally to fluid separation devices, systems, and methods, and more particularly, to fluid separation devices, systems, and methods employing membraneless separation components for processing fluids, such as blood.

BACKGROUND

Extracorporeal processing of blood is known to have many uses. Such processing may be used, for example, to provide treatment of a disease. Hemodialysis is the most commonly employed form of extracorporeal processing for this purpose. Additional uses for extracorporeal processing include extracting blood components useful in either treating others or in research. Apheresis of plasma (i.e., plasmapheresis) and thrombocytes, or platelets, are the procedures most commonly employed for this purpose. Also, non-therapeutic devices have been developed to analyze blood which may involve extraction of blood components. For example, some devices can separate blood and plasma, or specific analytes, for purposes of diagnosis.

BRIEF DESCRIPTION OF DRAWINGS

Where appropriate, like reference numbers have been used to indicate like elements in the figures. Unless otherwise noted, the figures have not been drawn to scale.

FIG. 1A is a schematic diagram of cross-section A-A of the membraneless separation device of FIG. 1B.

FIG. 1B is a schematic diagram of a membraneless separation device according to an embodiment of the disclosed subject matter.

DETAILED DESCRIPTION

Figure 1C:
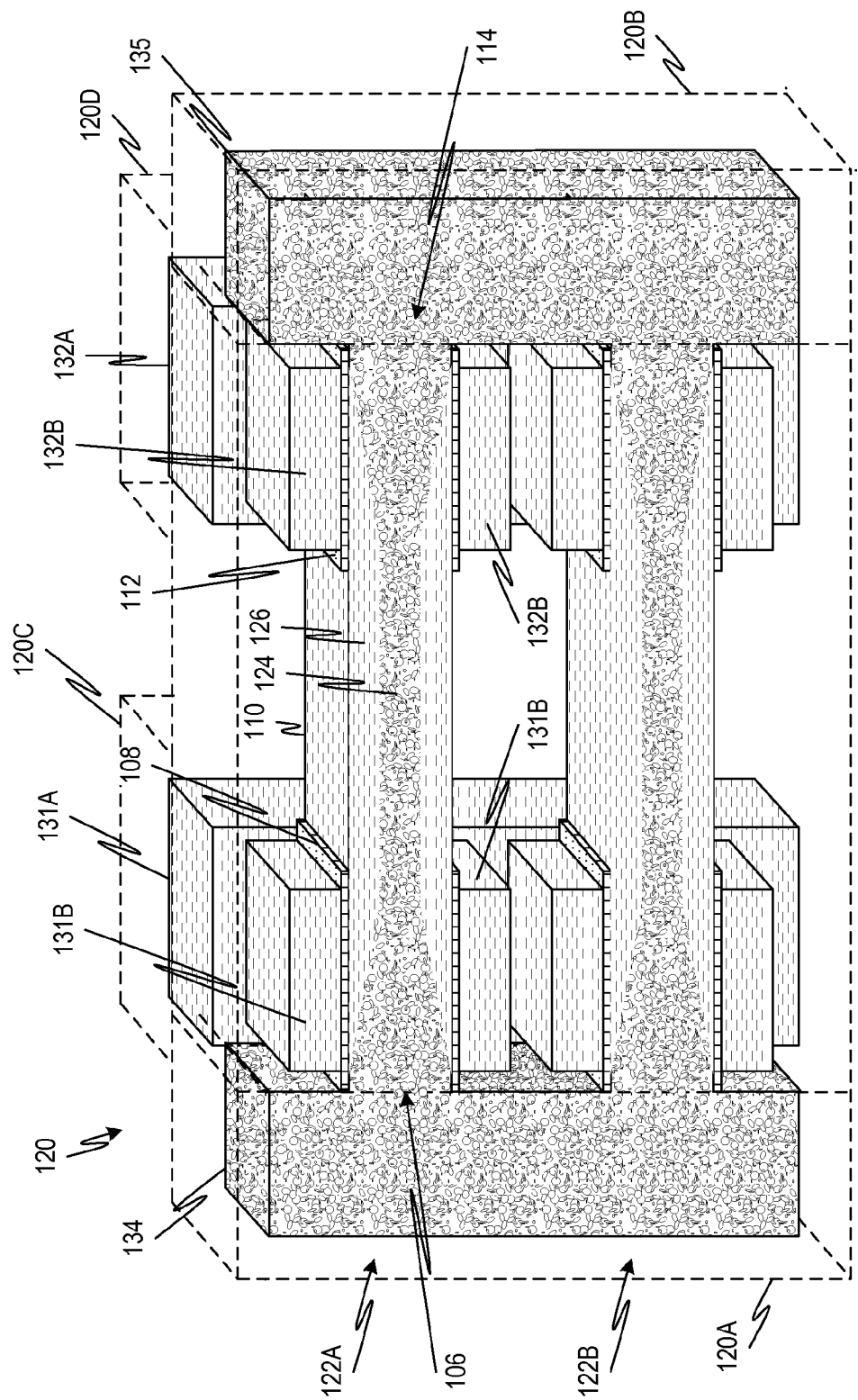
FIG. 1C is a schematic diagram showing sample and extraction fluid flows in the membraneless separation device of FIG. 1A.

A blood treatment for a patient can include separating blood components into a cytoplasmic body-depleted blood fluid fraction ("CBF;" that is, fractions that are depleted of, or free of, cytoplasmic bodies such as leukocytes, erythrocytes, and platelets (thrombocytes)) and a remaining blood fraction using a primary membraneless separation device and performing a treatment on the CBF. The use of a membraneless separation device permits the treatment to be done without anti-coagulants or with lower quantities of anti-coagulants. The embodiments disclosed include one or more treatments applied to CBF with or without anti-coagulants. For patients with ESRD, the treatments can include one or more of ultrafiltration, hemodialysis, hemofiltration, and hemodiafiltration, photopheresis, sorbent-based dialysis, chemical, mechanical (e.g., centrifugation), or any other type of treatment which may be facilitated or modified by performing it on a CBF rather than blood or a blood component prepared by other means. The primary membraneless separation device can be used in conjunction with an extraction fluid treatment device to provide the desired treatment on the CBF.

In embodiments, the use of a membraneless separation device reduces and/or minimizes contact between cytoplasmic bodies, such as the patient's blood cells, and artificial surfaces, such as the semi-permeable membrane of a conventional dialyzer, which is fundamental to current hemodialysis equipment. Such a reduction in artificial surface exposure may improve clinical outcomes and reduce or eliminate the need for anti-coagulants during treatment.

The devices, system, and methods described herein selectively transfer molecular components from a sample fluid such as blood by contacting the sample fluid with another fluid, identified as an extraction fluid. As discussed in U.S. patent application Ser. No. 11/127,905 (published as U.S. Patent Application Publication No. 2006/0076295) to Leonard et al., filed May 12, 2005, hereby incorporated by reference in its entirety as if fully set forth herein, flow patterns and species exchanges occur when blood is flowed as a thin layer adjacent to, or between, concurrently flowing layers of an extraction fluid, without an intervening membrane (i.e., membraneless). In the '905 application, the extraction fluid is identified as a sheath fluid, a sheathing fluid, extractor fluid, and a secondary fluid. The extraction fluid, moreover, is generally miscible with blood and diffusive and convective transport of all components is expected.

As taught in U.S. patent application Ser. No. 11/814,117 (published as International Publication No. WO 2007/137245) to Leonard and filed May 22, 2007, hereby incorporated by reference in its entirety as if fully set forth herein, a microfluidic flow channel capable of separating cytoplasmic bodies from other components may employ filters such as nanoporous membranes with precise, short pores and high void fractions. In the '117 application, the extraction fluid is identified as a secondary fluid, a miscible fluid, and an extraction fluid. The embodiments of microfluidic separation channels with such wall filters described in the '117 application may be employed in, for example, in the walls of, any of the microfluidic separation channels described in the present application.

By using a microfluidic device, components of blood can be separated for further processing. The microfluidic device may have channels with a height ranging between 0.5 to 1.5 mm and preferably in the range of 0.7 to 1.3 mm, where "height" is the dimension perpendicular to the direction of flow and perpendicular to the interfacial area across which transport occurs. In embodiments, there is no extraction fluid and the channels are used for separating blood into fractions that are depleted, and fractions that are enriched, in cytoplasmic bodies such as cells and platelets.

Sheathing a core of blood with a fluid (sometimes referred to herein as an "extraction fluid" to identify a function thereof), or assuring that the extraction fluid flows between at least a substantial portion of the blood and the enclosing boundaries of the flow path, prevents, or at least reduces contact of the blood with these boundaries. In turn, this configuration of the two fluids prevents or at least reduces undesirable activation of factors in the blood, thereby reducing bioincompatibilities that have been problematic in other techniques of blood processing.

The devices, systems and methods described herein also have the benefit of being capable of selecting various blood components of different sizes. In particular, the flow of blood, and an extraction fluid with which it is in contact, can be controlled for the purpose of achieving the desired separation of components (e.g., separating molecules of low molecular weight only). For example, as explained herein, various flow conditions may be used that cause cytoplasmic bodies (e.g., cells and platelets) to move away from the blood-liquid interface, thereby making it possible to "skim" the flow to remove substantial amounts of CBF or plasma. The outlets of the device can be arranged to capture the separated CBF or plasma along with the extraction fluid (if any), thereby providing a CBF component to, for example, a secondary processor. In embodiments, the channel is fitted with wall filters, as described in U.S. patent application Ser. No. 11/814,117 incorporated by reference above and described hereinbelow, to block the flow of any entrained cytoplasmic bodies in the CBF and configured to permit blood to sweep the cytoplasmic bodies from surfaces thereof.

Separation of CBF from a sample fluid (e.g., blood) occurs under conditions that inhibit and/or prevent advective mixing of the sample fluid and the extraction fluid. Advection describes the transport of fluid elements from one region to another, and is used to distinguish disordered convection from diffusion unaided by convection or diffusion in the presence of only ordered and unidirectional convection. The term advection is therefore used to indicate a form of transport within a fluid or between two contacting miscible fluids in which subvolumes of fluid change their relative locations, ordinarily occurring as a stage in mixing. Advection can occur in turbulent flows or in unstable laminar flows. Advective mixing, moreover, is often purposefully induced by the application of a moving agitator to a fluid. The inhibition and/or prevention of advective mixing and the short contact times that lead to small areas of contact (and, in turn, to a small device that has a small size and a limited fluid volume) is greatly facilitated by the use of a microfluidic geometry for the channel of the membraneless separation device.

Membraneless contact of a thin layer of blood with an extraction fluid may be used to cause high rates of exchange per unit area of contact between blood and extraction fluid for all solutes, but with discrimination among free (unbound) solutes that is less than the square-root of the ratio of their diffusion coefficients. While high exchange rates (e.g., of toxic substances) are often desirable, indiscriminate transport is not. Therefore, according to the principles of the present disclosure, a membraneless separation device as described herein may also be used in conjunction with at least one secondary processor (e.g., a membrane device or other type of separator) in order to restrict the removal of desirable substances and effect the removal of undesirable substances from blood.

The efficiency of such a secondary processor can be greatly increased by the use of the primary separation device, such as the disclosed membraneless separation device, which is capable of delivering plasma or CBF from a blood or blood component thereto. Therefore, transport of molecular components of blood to the extraction fluid in the membraneless separation device may be indiscriminate. The extraction fluid, carrying blood molecular components that are both desirable to remove (e.g., uremic toxins and drugs) and molecular components that should be retained (e.g., serum albumin) can be provided to the secondary processor such that the fluid entering the secondary processor is substantially free of cytoplasmic bodies. The secondary processor, meanwhile, regulates the operation of the membraneless separation device through the composition of the recycle stream that it returns (directly or indirectly) to sheath fluid inlets of the membraneless separation device.

Moreover, a membrane-based secondary processor operating on a CBF from blood is able to achieve much higher separation velocities because concentration polarization (i.e., the accumulation of material rejected by the secondary processor on the upstream side of the separator) is limited to proteins and does not involve cytoplasmic bodies. Furthermore, because cytoplasmic bodies are retained in the primary separation device (i.e., the first stage membraneless separation device) by a sheathing flow, their contact with artificial material is reduced at least in part due to the sheathing by the extraction fluid. As such, it should be understood that the need for anti-coagulant may be greatly reduced or eliminated. In addition, a membrane-based secondary processor used in this manner may achieve much higher separation velocities because cytoplasmic bodies, such as cells, which may be susceptible to shear, are not present.

While it should be clear that the membraneless exchange device is applicable to dialysis treatments, for example, hemodialysis and ultrafiltration, the membraneless exchange device is also useful in other situations where a sample fluid is to be purified via a diffusion mechanism against another fluid (e.g., an extraction fluid).

The relative thicknesses (or mass flow rates) of the sheath flow versus the blood or sample fluid can vary depending on the application and other criteria. Ratios that favor extraction fluid may underutilize the extraction fluid's capacity to accept molecules diffusing into it. Ratios that favor the sample fluid or blood may saturate the extraction's fluid's capacity to accept molecules diffusing into it, thereby potentially undertreating the sample fluid or blood for each unit of mass thereof passed through the membraneless exchange device. In embodiments, the ratios of sample fluid (e.g. blood) to extraction fluid are in the range of 1:3 to 3:1. In particular embodiments for blood treatment the ratio is approximately 1:1. Blood flow may be in the range of, for example, 0.5 ml/second to 5 ml/second during a blood treatment.

As described herein, a flow of blood, or blood fluid, may be completely or partially surrounded by another liquid (e.g., extraction fluid) such that the streams are contacted in a microfluidic channel and are subsequently separated at the end of the channel. The middle stream, substantially the whole blood or blood fluid, is thus sheathed by, or surrounded by, extraction fluid. The contact between the co-flowing fluids occurs along a flow path whose cross-section is either rectangular, preferably of great breadth and limited thickness, or circular. Other cross-sections for the flow path may also be possible. For example, the cross-section may be circular, elliptical, oval, trapezoidal, or rectilinear with rounded corners, as long as the shape is consistent with the required flow dynamics.

The requisite interfacial areas can be achieved by combinations of channel length, width, and number according to the principles described herein. In particular, Area=2 (top and bottom)×width×length×number of channels stacked or otherwise arrayed in parallel. As used herein, the term "width" refers to a dimension perpendicular to the direction of flow and parallel to the interface between the two liquids, while, as explained above, the term "height" refers to a dimension perpendicular to the direction of flow and also perpendicular to the interface between the two fluids. The competing requirements of small height (to avoid excessive diffusion times and in-process volumes), short length (to avoid excessive pressure drop) and practical limitations on width of a single device suggesting the need to array the extraction channels in parallel, side-by-side or in a stack can be satisfied in practical microfluidic devices.

The contact area of the various embodiments will depend on the particular details of the application. Factors include fluid flow rates of blood and extraction fluid and their relative rates, treatment times, the type and amount of blood components desired to be removed in a given treatment session, and frequency of treatments. An example embodiment has a blood flow of at least about 20-30 ml/min and a contact area of at least about 1000 cm$^2$. The contact areas can vary from these base levels by more than an order of magnitude. Also, the blood flow rates can be several time higher.

Referring now to FIG. 1A-1C, a membraneless separation device 120 employs at least one extraction channel 110, and preferably, multiple extraction devices 122A, 122B, each with a respective extraction channel 110. As shown, the multiple extraction devices 122A, 122B can be formed in a layered structure to achieve compactness. Although only two extraction devices 122A, 122B are illustrated in FIG. 1A, any number of extraction devices 122A, 122B can be provided.

An extraction fluid and a sample fluid can be passed in laminar flow through a common extraction channel 110. The flow in the extraction channel 110 is such that the extraction fluid and sample fluid come into direct contact, but remain in defined layers throughout the common extraction channel, as shown in FIG. 1C. Thus, a layer of sample fluid 124 is separated from the walls of the extraction channel 110 by extraction fluid layers 126, as shown. Each extraction channel 110 can have dimensions that assure laminar flow conditions are maintained even under conditions of normal use and that permit a large interface area between the sample and extraction fluids in a compact design.

The flow in the extraction channel 110 creates two liquid-liquid boundaries between the sample fluid layer 124 and the two extraction fluid layers 126. The extraction channel 110 can be configured so that it substantially isolates the sample fluid layer 124 from the artificial walls of the extraction channel 110 while the sample fluid layer 124 is in the extraction channel 110. For example, the extraction channel 110 can be many times wider and longer than it is deep. As a result, the sample fluid layer 124 contacts the extraction fluid layer 126 over a large area (length×width), but contacts the artificial walls of the channel 110 over a much smaller area at the lateral edges of the extraction channel 110. This helps to provide a large interface between the sample and extraction fluids and effectively isolates the sample fluid from the walls of the extraction channel 110.

The extraction channel 110 can have extraction fluid inlets 108 which convey the extraction fluid from extraction fluid inlet channels 131B into the extraction channel 110 adjacent the walls. The extraction channel 110 can include respective extraction fluid outlets 112, displaced in a length direction from the inlets 108, which draw extraction fluid from the extraction channel 110 and convey to extraction fluid outlet channels 132B. As shown in FIG. 1A, a common extraction fluid supply line 137, for example, from a common pump or processor outlet, provide extraction fluid to an inlet header 120C so as to distribute extraction fluid to respective plenums 131A for distribution to the extraction fluid inlet channels 131B. Similarly, an outlet header 120D connected to a common extraction fluid removal line 138 can remove extraction fluid from extraction channels 110 via the extraction fluid outlet channels 132B and respective plenums 132A. Other fluid distribution schemes for directing extraction fluid to and from the extraction channels 110 can also be employed.

Each extraction fluid outlet 112 can be provided with a respective filter 136, such as a nano-pore filter, as described in more detail below. Each extraction fluid inlet 108 can also be provided with a respective filter 128, such as a nano-pore filter. If provided, the filters can have a pore size of, for example, less than although other pore sizes are possible according to one or more contemplated embodiments.

The sample fluid can flow into a sample fluid inlet 106 of the extraction channel 110. An aligned sample fluid outlet 114 can be provided for exit of the sample fluid from the extraction channel 110. A common sample fluid supply line 102, for example, from a pump or a patient line, can provide sample fluid to an inlet header 120A for distribution to plenum 134 and on to each sample fluid inlet 106. Similarly, an outlet header 120B connected to a common sample fluid removal line 104 can remove sample fluid from extraction channels 110 via sample fluid outlets 114 and respective output plenums 135. Other fluid distribution schemes for directing sample fluid to and from the extraction channels 110 can also be employed.

The extraction fluid inlet flow paths 132B and sample fluid inlet plenum 134 can be configured to allow for introduction of the respective fluids into the extraction channel 110 in a manner so as to minimize disruption to the interface between the extraction fluid layer and the sample fluid layer. Although the configuration of the inlets 106, 108 and outlets 112, 114 has been shown in FIG. 1A-C with a particular shape, other configurations for and number of inlets and outlets are possible.

The extraction channel 110 can be usable for renal replacement therapy, for example, for a patient with ESRD. In such a configuration, the sample fluid can be blood and the extraction fluid can be an aqueous solution, such as saline or dialysate. The cytoplasmic bodies tend to remain in the sample fluid layer as compared to smaller particles, such as proteins, ionic species, and/or other unwanted components. The cytoplasmic bodies can thus be isolated in the middle of the extraction channel 110 so as to reduce and/or minimize their contact with artificial channel surfaces. In a renal replacement therapy embodiment, it is contemplated that only components free of cytoplasmic bodies of the blood are extracted by the extraction channel 110.

The cytoplasmic bodies may be collected at the extraction channel outlet 114 and returned to the patient. The extraction fluid may be collected from the extraction channels outlets 112 and directed, for example, to a secondary processor by way of extraction fluid outlet channels 132B and header 120D. Cytoplasmic bodies, or other large particles, can be blocked from exiting the extraction fluid outlets 112 into the extraction fluid outlet channels 132B by filters 136, which are also described in more detail below.

Transport of molecules within the extraction channel 110 is governed by diffusion and the flow is non-turbulent with no mixing or advection of the flow. Mixing between the sample and extraction fluid flows is prevented by appropriately selecting flow rates based on the flow channel dimensions of the membraneless separation device and the flow rates. When configured to function as a dialyzer, the membraneless separation device can enable treatments with brief contact time between blood and artificial materials, low extracorporeal blood volume, and very compact size in a microfluidic device. Note that as used herein, the term "extracorporeal" is not necessarily limited to the removal of blood from the patient body envelope. Microfluidic extraction channels that are implanted in the bodies of patients are not intended to be excluded from the scope of the present disclosure.

The flow of extraction fluid in the extraction channel 110 can be controlled independently of the flow of sample fluid in the extraction channel 110 using an appropriate combination of one or more injection pumps and withdrawal pumps. For example, a first injection pump can inject extraction fluid through extraction fluid inlet channels 131B and into the extraction channel 110 and a first withdrawal pump can withdraw extraction fluid out of the extraction channel 110 through extraction fluid outlet channels 132B. Similarly respective injection and withdrawal pumps can inject and withdraw sample fluid into and from the extraction channel 110, respectively.

By controlling the relative rates of the pumps and the pressure drop along various points in the fluid circuit, the change in total volume of the sample fluid exiting the extraction channel 110 can be varied. Thus, in the use of the membraneless separation device in the treatment of blood, the control of the inflow and outflow rates can be used to regulate a patient's fluid volume, which is a conventional requirement of renal replacement therapy.

For a membraneless separation device configured for the treatment of blood, the extraction channel 110 depth (or height) can be in the range of 700 µm to 1300 µm, although depths below this range are also possible according to one or more contemplated embodiments. The extraction channel 110 can have a width-to-depth ratio of at least 10. For example, the width-to-depth ratio of the extraction channel 110 can be greater than 50 and preferably greater than 500. Note that although the figurative depictions herein show a particular number of pumps, other embodiments can employ a smaller or greater number of pumps.

For a number of reasons, an extraction channel 110 that relies solely upon the differences in the diffusion rates of small versus large particles (that is, small molecules versus macromolecules or even cytoplasmic bodies) may not be sufficiently discriminating to provide a basis for blood treatment. For example, a practical system for renal replacement therapy preferably inhibits and/or prevents the sample fluid retrieved from outlet 114 from being depleted of a significant fraction of the macromolecules, such as serum albumen, entering at inlet 112. In addition, the system can also inhibit and/or prevent the loss of blood cells. Thus, additional features can be combined with the extraction channel 110 to enable the benefits of a membraneless separation device but with the high degree of discrimination normally associated with membranes.

In blood treatment embodiments, the extraction fluid provided to extraction channel 110 can occupy approximately ⅔ of the cross-section of extraction channel 110, with blood from a patient arranged in the middle ⅓. This configuration can be maintained by appropriately regulating the inflow of blood and extraction fluid. In this configuration, each half of the blood layer in extraction channel 110 is "serviced" by one of the extraction fluid layers, and the extraction fluid layers are traveling at an average velocity that is approximately half that of the blood, though the interfacial velocities of the blood and extraction fluids are approximately equal. Thus, the volume of blood and the volume of extraction fluid that pass through the unit in a given period of time are approximately equal. While not limited in this manner, it should be noted that, in the configurations described herein, the exchange efficiency drops, from the maximum of 50% associated with equilibrium, when the volumetric flows of the two fluids (e.g., blood and extraction fluid) are different from each other.

Figure 1D:
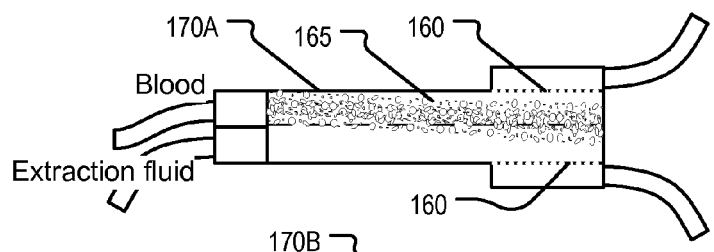
FIGS. 1D-1F illustrate various membraneless channel configurations and shapes.
Figure 1E:
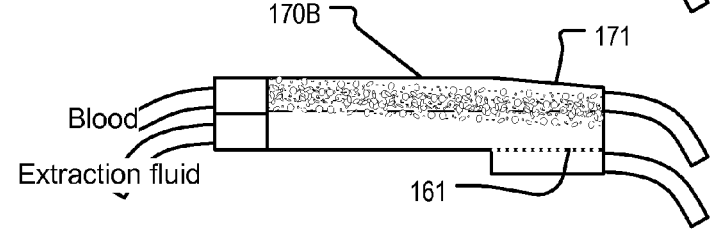
Figure 1F:
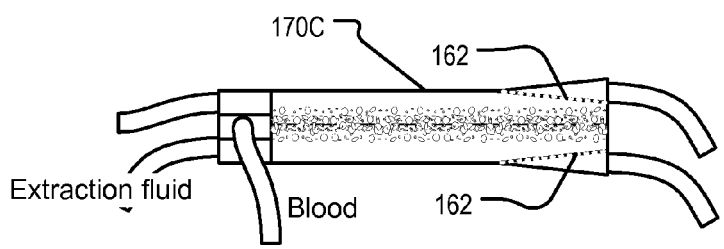

FIGS. 1D-1F illustrate various membraneless channel configurations and shapes. FIG. 1D is a figurative illustration of a membraneless separation channel 170A in which blood or sample fluid is injected into one side and extraction fluid into an opposite side. The flow is therefore non-sheathing. The cytoplasmic bodies in the flow migrate to the lowest shear portion of the flow, permitting CBF and extraction fluid, if present, to be skimmed at an outlet 160 with (or without) a nanoporous filter. The CBF can be extracted on both, or a single side, as illustrated. FIG. 1E shows an embodiment of a membraneless separation channel 170B in which the walls of the generally rectilinear channel are not precisely parallel. The wall 171 is sloped such that the channel narrows slightly near the outlet 161 of the channel. In alternative embodiments, the shape of the channel can depart from rectilinear. In some embodiments, the variance from parallel walls is such that substantially no flow reversal or mixing effect can occur in the channel itself. In FIG. 1F, the channel walls at outlets 162 converge on both sides of the channel. Since fluid is taken off at the channel outlets, the convergence of embodiments shown in FIG. 1E and FIG. 1F may help to maintain stability in the interface between the cytoplasmic body-containing portion of the flow and the extraction portion of the flow.

Figure 2A:
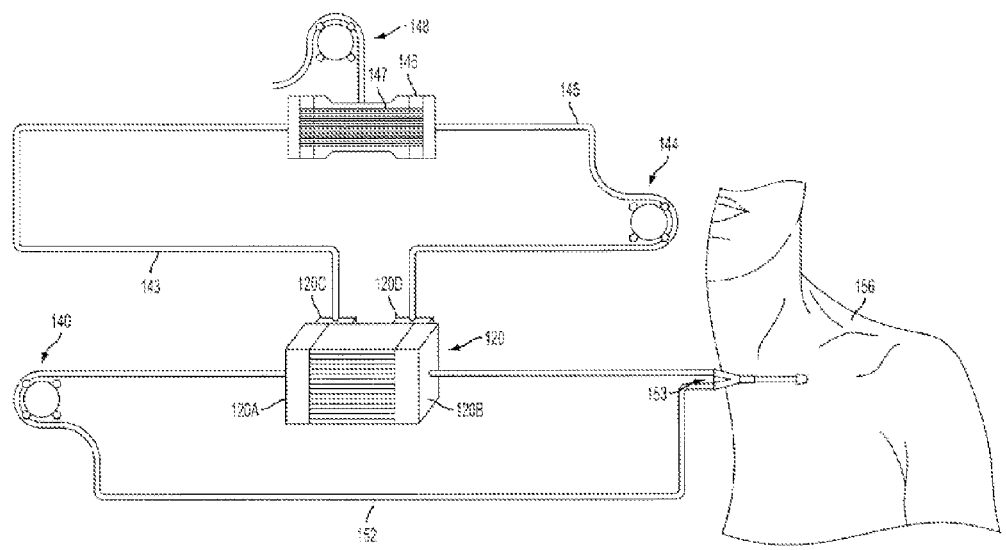
FIG. 2A is a schematic diagram of a membraneless separation device employing two pumps and showing features of an ultrafiltration embodiment.

FIG. 2A is a schematic diagram of a membraneless separation device employing two pumps and showing features of an ultrafiltration embodiment. In this embodiment, a blood pump 140 pumps a sample fluid, blood, or a blood fluid into a membraneless separation device 120 along an inlet. When the sample fluid is blood, a central access 153 connected to a patient 156, for example, a catheter attached to the subclavian artery of patient 156, can be provided to supply blood to blood pump 140 along a blood inlet line 152 as well as to return blood from the outlet header 120B of membraneless separation device 120 to the patient 156. Although shown connected to a person in the Figures, it is of course contemplated that the membraneless separation device may be connected to a blood supply/reservoir and/or a living animal.

Similar to membraneless exchange separation 120 described above with respect to FIGS. 1A-1C, the configuration illustrated in FIG. 2A can include multiple extraction channels 110 arranged in parallel. Each extraction channel 110 can be used to extract a portion of the plasma from the flowing blood for ultrafiltration. For example, plasma from the blood entering extraction channel 110 through inlet header 120A can be skimmed and exit with the extraction fluid through outlet flow paths 132B.

An ultrafilter 146 with a membrane 147 (e.g., tubular filter fibers) can convey processed extraction fluid back to the membraneless separation device through tubing 143 whilst allowing the removal of ultrafiltrate from the extraction fluid by an ultrafiltrate pump 148. In this configuration, the extraction fluid pump 144 in combination with an ultrafiltrate pump 148 cooperatively control the flow of extraction fluid into the membraneless extraction channel 110 and the net extraction of ultrafiltrate from the ultrafilter 146. These in turn determine the net flow of CBF from the sample or blood fluid into the extraction fluid flow out of the extraction channel. The use of pump 148 to remove ultrafiltrate is not necessarily required. Rather, pressure induced by the flow through ultrafilter 146, such as the pressure generated by pump 144, may be sufficient to pass the ultrafiltrate through membrane 147 for removal.

Pumps 140 and 144 (or other possible pump arrangements) can be used to control the flows of the extraction fluid and sample fluid (e.g., blood) so as to withdraw only the extraction fluid or the extraction fluid plus a prescribed amount of sample fluid through extraction fluid outlet channels 132B. Likewise, pumps 140 and 144 can be controlled to regulate the flows of the extraction fluid and sample fluid to regulate the contact between the cytoplasmic body-containing sample layer and filters in extraction fluid outlets 112.

Control of the extraction and sample fluid flows can be such that water volume to be drawn down from a patient is performed at as low a rate as possible. Therefore, the net draw-down of water volume can be accomplished over a maximum duration consistent with the desired treatment time and patient requirements. The water draw-down can be accomplished by drawing a larger volume through the extraction fluid outlet channels 132B than replaced through the extraction fluid inlet channels 131B. Thus, the pumps can be controlled to reduce and/or minimize the difference in outlet and inlet flow rates and to regulate the two rates precisely. By precisely regulating the mean and instantaneous flow rates, the interface between the center cytoplasmic body-containing layer and the fluid outlets can be maintained to ensure that a minimum of cytoplasmic bodies contact the extraction channel 110 walls or any filters in the outlets.

The types of pumps that can be employed in the disclosed systems are not limited to those illustrated in the figures. Rather, any type of fluid pump known in the art can be used. Moreover, although the roller pumps illustrated in the figures are shown with four rollers, fewer or additional rollers are also possible according to one or more contemplated embodiments. It should be understood that embodiments are not limited by the particular types of pumps or flow rates, and it should be clear that many variations are possible.

In order to cause the separation (or skimming) of CBF, the inlet and exit flows of the extraction fluid can be controlled such that more total fluid is withdrawn from extraction channel 110 through extraction fluid outlet channels 132B than extraction fluid provided through extraction fluid inlet channels 131B. Thus, a CBF portion of the blood being processed is removed along with the extraction fluid through extraction fluid outlet channels 132B. This portion can be pumped via pump 144 to an ultrafilter 146 by way of tubing 145. The ultrafilter 146, employing a membrane 147 and ultrafiltration pump 148, can extract ultrafiltrate from the removed CBF portion of blood (plus extraction fluid) before recycling the processed CBF portion of blood to the membraneless exchange channel 110 by way of tubing 143.

It should be understood that operation of extraction channel 110 that allows the sheath exit flows to be larger than the corresponding inlet values will induce a convective flow from the blood stream, over and above the diffusive flow. In order to inhibit and/or prevent such a convective flow from carrying blood cytoplasmic bodies with it (as would be the case if the distribution of cytoplasmic bodies in the blood stream was uniform), it is desirable that cytoplasmic components of the blood have migrated to the center of the blood stream in order to permit significant plasma skimming. The drift of cytoplasmic bodies may occur under a variety of flow regimes. The flow conditions can be adjusted to cause cytoplasmic bodies to move away from the blood-liquid interface. For example, when blood flows in a tube below a wall shear rate (measured as the blood-flow velocity gradient perpendicular to the tube wall) of about $100\ s^{-1}$, this shear rate cytoplasmic components to migrate to the center of the tube. Thus, the occurrence of contact of cytoplasmic bodies with the filters is reduced.

Long-term stability is desirable for satisfactory operation of the microfluidic devices described herein. For example, it may be desirable to inhibit and/or control differences in sheath inlet and outlet channel flows, which, uncorrected, can result in unintended infusion of extraction fluid into or out of the bloodstream. In addition, it may be desirable to maintain the stability of the interface between the sample fluid or blood fluid and the extraction fluid. Accordingly, on-board electronics and photonics (not shown), which are common features of chip-based microfluidic devices, can be used to regulate the system (e.g., to introduce flow changes) with an electrically activated device (e.g., a piezoelectric valve) that is mounted on the same plate, or "chip," on which extraction channel 110 is located. In addition, mechanical devices such as buffer chambers, elastic bladders, compliant tubing lengths, and such features, including choices of materials, can be sized and otherwise configured to ensure that volume-flow variations and pressure pulses do not propagate into the separation channel and cause undesirable advection.

Controls can be provided to ensure stability of the fluid flows. For example, a control system can be provided which shuts down the system and initiates an alarm when cytoplasmic bodies are detected in the extraction fluid outside the membraneless separation device or when independent flow measuring sensors detect a flow imbalance between blood and net extraction fluid flows beyond a threshold imbalance, which might occur when a prescribed quantity of plasma is removed or when hypervolemia is being treated.

Figure 2B:
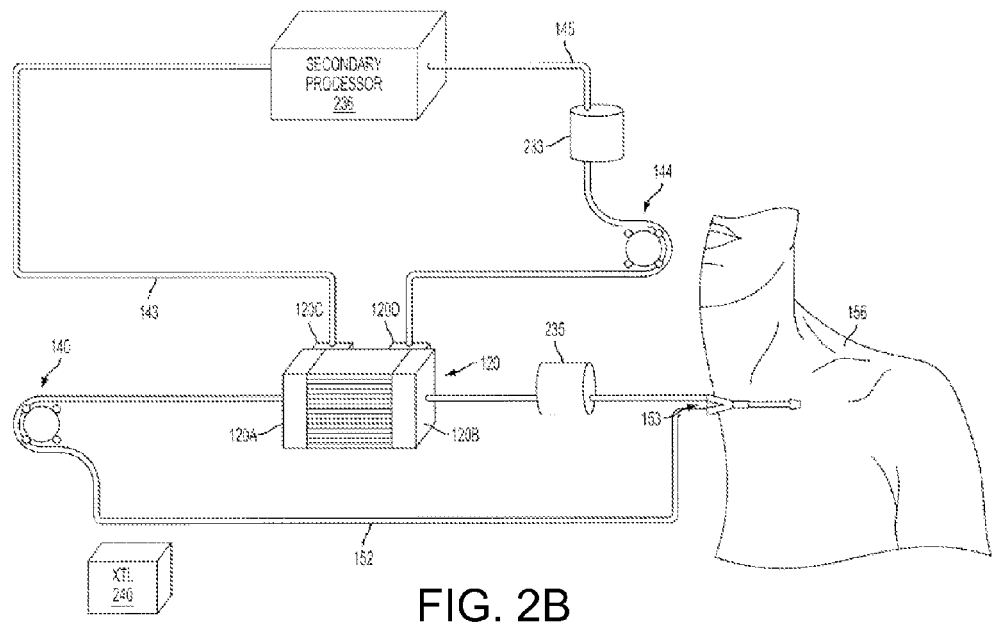
FIG. 2B is a schematic diagram of a membraneless separation device integrated with a secondary processing unit for treating a patient according to an embodiment of the disclosed subject matter.

Similar to FIG. 2A, FIG. 2B illustrates a configuration of a membraneless separation device 120 employing multiple membraneless extraction channels 110. However, in contrast to FIG. 2A, the ultrafilter 146 has been replaced with a secondary processing unit 236.

The secondary processing unit 236 can include a variety of mechanisms for treating the extraction fluid or CBF, including ultrafiltration, sorption using a wide range of sorbents targeted to particular small and large molecules, catalysts, dialytic regeneration and optical treatment (photopheresis). Plasma diafiltration may also be used to remove low-molecular weight solutes by introducing a stream of sterile buffer to the blood to allow a greater volume of fluid, with its accompanying small molecules which pass through a diafiltration membrane. In conventional diafiltration, this volume of sterile buffer may be added before or after the diafilter. It is advantageous to add it either to the bloodstream or the recycle fluid from the secondary separator, which is the primary source of extraction fluid. The secondary processor 236 can employ a variety of mechanisms to treat the received extraction fluid such that a desired interaction with the sample fluid is achieved. In addition to ultrafiltration, diafiltration, and dialysis, these mechanisms can include, but are not limited to, sorption, using sorbents targeted to particular small and/or large molecules, chemical reaction, and precipitation. The following international publications describe examples of suitable hemodiafilters for use as the secondary processor: International Publication No. WO 2002/62454 to Collins et al., filed Feb. 7, 2002; International Publication No. WO 2002/45813 to Collins et al., filed Dec. 7, 2001; and International Publication No. WO 2002/36246 to Collins et al., filed Oct. 30, 2001.

The treatment to which extraction fluid is subjected in the secondary processor can be substantially the same as those performed in the various types of conventional treatment using whole blood or cytoplasmic body-free plasma. A secondary processor can include any of a variety of devices used for refreshing the extraction fluid. For example, a membrane device or a sorption device can be used. In addition, the extraction channel and secondary processor system is not limited to renal replacement therapy applications. For example, such a system can also used to remove, destroy or inactivate a substance related to a specific disease. Examples include enzyme reactors, cryoprecipitators, and/or ultraviolet irradiators. The system can also be used for extracting components from a non-blood sample fluid, in which a secondary processor receives the extraction fluid and at least some of the components of the sample fluid which are not to be removed.

The secondary processor 236, working in conjunction with the membrane separation device 120, will automatically tend to balance the outflow of macromolecules from the extraction channels 110 against the inflow of macromolecules which have been retained by the secondary processor 236 and conveyed back to the extraction channels in membraneless separation device 120 along tubing 143. Thus, the secondary processor 236 regulates the operation of the extraction channels 110 through the composition of the recycle stream that it returns to the extraction fluid inlet channels 131B of the extraction channel 110.

In blood therapy, one example of a macromolecule which it is desirable to retain in the blood is serum albumin. In each pass through a diffusion-based exchange device, such as the extraction channel embodiments described, albumin may diffuse at no more than ¼th the rate of small solutes. However, in a renal replacement therapy treatment, a given volume of blood must pass multiple times through the exchange device in order to remove urea and other low molecular weight metabolic waste solutes from the body because they are distributed throughout the total body water compartment. Urea is considered a proxy for all such low molecular weight metabolic waste solutes, and is easy to measure. Thus, urea must be picked up from the tissue by a urea-depleted volume of blood and passed to the extraction fluid to be replenished, whereupon the same volume, perhaps ten times in a treatment, returns to the tissues to pick up more urea and deliver it to the extraction fluid. So while albumin diffuses slowly compared to urea, a given molecule of albumin has many more opportunities to be picked up by the extraction fluid. As a result, the fractional removal of albumin, even though its inherent diffusion rate is smaller, may tend to exceed the fractional removal of urea.

The secondary processor (e.g., a membrane device that permits extraction of urea and water but not albumin) can be used to ensure against the removal of albumin to the blood by returning it in the extraction fluid processed by the secondary processor. In contrast, urea is removed from the extraction fluid by the secondary processor and extraction fluid is returned to the extraction channel, depleted of urea. The refreshed extraction fluid is therefore able to pick up more urea in the extraction channel. As mentioned, the returning stream of extraction fluid may also have a selected water content as well. Thus, the composition of this stream will recruit the further extraction of urea and water but will not recruit further extraction of albumin, given that the difference in albumin concentration between the blood being processed and the extraction fluid will have disappeared.

The difference between the inlet flow rate and the outlet flow rate of the extraction fluid can be controlled to control the compositions of the exiting sample and extraction fluid streams. In renal replacement therapy, if the rate of outflow of the extraction fluid from the extraction channel is equal to its rate of inflow, even when urea is removed by the secondary processor, a net flow of albumin and other macromolecules into the outgoing extraction flow will automatically be balanced by a net inflow back into the sample (blood) stream. If there is a higher fluid volume rate of removal from the extraction channel from the rate at which fluid is returned to the extraction channel, the patient's water volume will be reduced by the water draw-down. The concentration in the extraction flow, which is a closed loop, increases until the concentration of macromolecules, including albumin, rises in the recycle stream to match the level in the sample stream such that a transport balance is maintained and no net loss of such components is obtained, except for any component which may remain in the extracorporeal circuit after treatment is terminated.

The system shown in FIG. 2B can also include an extraction fluid reservoir (not shown). The extraction fluid reservoir can provide a supply of fresh extraction fluid (e.g. such as replacement fluid used in hemofiltration or dialysate for preferred blood treatment embodiments) to the flow loop between membraneless separation device 120 and secondary processor 236. Under normal operation of some embodiments, components of the blood fluid that have diffused into the extraction fluid are removed by secondary processor 236. Under certain conditions, certain blood components, such as fibrinogen, that diffuse into the extraction fluid from the blood fluid may collect along the surface of filters in the outlets. These materials can be removed from the surfaces of filters in the outlets by temporarily reversing the flow of the extraction fluid to flush the filters using only a small quantity of extraction fluid. This amount of extraction fluid can be replenished from extraction fluid reservoir upon reestablishing normal co-current flow of extraction fluid relative to the blood fluid. The need to perform this "blowback" operation can be determined by pressure drop across the filters or flow measuring devices. These devices can be integrated into the system of FIG. 2B. The extraction fluid reservoir can also serve as a source of replacement fluid for treatments, where more water and solute volume are deliberately eliminated in the secondary processor than are to be eliminated from the patient for treatment purposes, as is done in hemofiltration, for example. Pumps 140, 144 can be automatically controlled by a controller 240, which can include a programmable processor.

As explained above and elsewhere herein, when indiscriminate plasma removal is not desired, the plasma that is skimmed from the blood using membraneless separation device 120 is processed by secondary processor 236, which regulates the operation of the extraction channel 110 through the flow rate and composition of the recycle stream that it returns to extraction fluid inlet channels 131B (i.e., a recycle stream is used to limit transport of blood components for which extraction is not desirable). A substantial benefit arises because secondary processor 236 is able to achieve high filtration velocities due to the fact that concentration polarization is limited to proteins and does not involve cytoplasmic components. Moreover, because cytoplasmic bodies are retained in extraction channel 110, through the action of cytoplasmic body migration and optionally supplemented by the action of the filters in the outlets, a majority of these cytoplasmic bodies would see artificial material only on its conduit surfaces. While some relatively small amount of cytoplasmic bodies may contact the filters in the outlets, the contact is limited to a small fraction of the total number of cytoplasmic bodies and occurs for a relatively short time. Because cytoplasmic body contact on the liquid-liquid contact area is far less traumatic, mechanically and chemically, a reduction in bio-incompatibilities and a reduced (or eliminated) need for anticoagulation is achieved. Additionally, because the primary transport surface in the system is intrinsically non-fouling and the surface of the filters is swept clean by the fluid shear rate, a major deterrent to long-term or continuous operation is removed, opening the possibility of a wearable and/or ambulatory system with the recognized benefits of prolonged, continuous, slow exchange.

The interface between the extraction fluid and the sample fluid, within the extraction channel, can be varied by adjusting the relative flow rates of the extraction fluid and the sample fluid. Additionally, a detector 233 may be placed in the extraction fluid outlet receiving stream or streams (e.g., flow exiting from outlet header 120D) to detect substances in the exiting fluid(s), for example, undesirable blood components in the exiting extraction fluid or within the extraction channel. A signal from the detector 233 may then be used to adjust the relative flow rates of sample and extraction fluids. Examples of such a detector include an opacity monitor and ultramicroscope arranged in the extraction channel and which can detect erythrocytes in the extraction channel outlet that should have received cytoplasmic body-free fluid. Alternatively, or additionally, a detector 235 can be arranged in the blood return line (e.g., inline with the flow exiting sample fluid outlet header 120B) to monitor the condition of blood flowing to the patient. For example, detector 235 can be a hemoglobin detector, which can indicate the rupture of cytoplasmic bodies due to improper fluid flows, or the onset of hypovolemia due to operating the system for too long. Total and relative extraction and sample fluid flow rates can be adjusted to correct such a condition. In another example, detector 235 can be a hematocrit sensor, an electrolyte sensor, a glucose sensor, a potassium sensor, or any other blood monitoring sensor commonly employed in the art.

Note that although in some discussions herein a single extraction channel and a single secondary processor are identified, it should be apparent to one of ordinary skill in the applicable arts that the use of singular nouns does not necessarily compel the use of only a single component. Rather, for example, multiple extraction channels and/or secondary processors can be used in a single device. Moreover, multiple extraction channels can be formed in a layered or folded structure to achieve compactness with high contact area between sample and extraction fluids. Additionally or alternatively, multiple extraction channels can be formed in a serial arrangement, with the outlet of one channel serving as the inlet for another channel.

As referenced above, the characteristics of the fluid flows can be controlled to cause cytoplasmic bodies to concentrate in the middle of the blood fluid stream. This reduces the amount of cytoplasmic bodies that diffuse into the extraction fluid, but some cytoplasmic body migration may still occur. Filters may be provided at the extraction channel outlets for the extraction fluid to inhibit and/or prevent cytoplasmic bodies from leaving the extraction channel with the extraction fluid. Accordingly, pores in the filters can inhibit and/or minimize departure of this small number of cytoplasmic bodies from the extraction channel with the extraction fluid. For example, the pores can have a diameter less than 1000 nm, preferably between 600 nm and 800 nm, which may inhibit cells from becoming lodged in the pores. Moreover, the high shear rates characteristic of microfluidic flows provide a shear force at the surface of the filter sufficient to "sweep" this surface. Because the numbers of cytoplasmic bodies in the extraction fluid are kept relatively low, this sweeping action facilitates keeping the surface of the filter clear of cytoplasmic bodies, thus aiding in the inhibition and/or prevention of clogging.

Similarly, other blood components can be inhibited from exiting the extraction channel with the extraction fluid. For example, the protein fibrinogen is capable of clotting, and it can be desirable in some embodiments to inhibit and/or prevent fibrinogen from exiting the extraction channel with the extraction fluid. Thus, the pores of the filters can be sized to keep fibrinogen in the extraction channel, for example, by using filters with a pore size of about 50 nm. In addition, fluid flow characteristics, fluid interface velocity, and fluid contact time can be controlled to complement the selection of pore size in inhibiting and/or preventing loss of certain blood components and in inhibiting and/or preventing fouling.

Various embodiments also eliminate or at least substantially reduce the fouling reactions that have been known to be a major deterrent to the continuous use of an extracorporeal separation device. In particular, as the primary transport surface in the membraneless separation device (also referred to herein as a membraneless exchange device, membraneless extraction device, and membraneless separator) can be intrinsically non-fouling because of the increased biocompatibility and because the interface is constantly renewed. Thus, a major deterrent to long-term or continuous operation is removed, opening the possibility to the design and construction of small, wearable devices or systems with the recognized benefits of nearly continuous blood treatment. Such a device or system can be very small and worn or carried by the patient (e.g., outside of a hospital or clinic setting), and can be supplied with external buffer reservoirs (in a back-pack, briefcase, or from a reservoir located in the home, located at the place of work, etc.). Further, because fouling would be reduced, and sustained operation at low blood flows over long times would be allowed, such anticoagulation as might be required can be administered as blood left the body and can be adjusted to have an effect confined to the extracorporeal circuit. As understood by those skilled in the art, avoiding systemic anticoagulation outside of the clinic is highly desirable.

Figure 3:
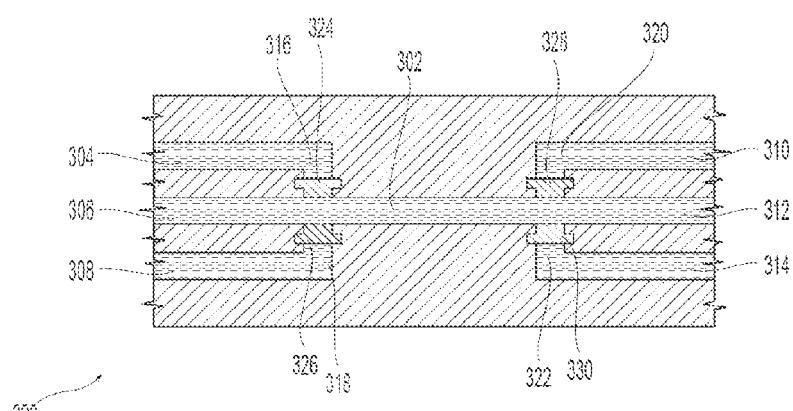
FIG. 3 is a schematic diagram of a membraneless separation device employing filters according to an embodiment of the disclosed subject matter.

FIG. 3 shows a membraneless separator 300 that is similar to the device 200 described above. The membraneless separator 300 includes an extraction channel 302, three separate inlet channels 304, 306 and 308 and three corresponding outlet channels 310, 312, and 314. Membraneless separator 300 has filters 324 and 326 placed in inlets 316 and 318, respectively, and has filters 328 and 330 place in outlets 320 and 322, respectively. The number of inlet or outlet channels used may be varied and filters may or may not be used in the inlets and outlets of the channel(s).

The membraneless separator 300 illustrated in FIG. 3 can be used as a plasmapheresis device. For example, plasma from the blood entering extraction channel 302 through inlet channel 306 can be skimmed such that it exits with extraction fluid through outlet channels 310 and 314. This process of skimming is accomplished by withdrawing a greater volume of extraction fluid from outlet channels 310 and 314 than is provided by inlet channels 304 and 308. Thus, this excess volume is removed from the blood fluid.

Since there is a tendency for cytoplasmic bodies to migrate toward the low-shear flow part of the extraction channel 302, a mixing layer between the sample fluid and the extraction fluid can be free of cytoplasmic bodies derived from the sample fluid. Thus, at least CBF from the sample fluid which enter the mixing layer can exit through the extraction fluid outlet channels 310 and 314. The extraction fluid may include a net gain in volume, thereby, since the mixing layer can be shared between the sample fluid outlet channel 312 and each of the two extraction fluid outlet channels 310 and 314.

It should be clear from the discussion herein, that the extraction channel 302 can be used to separate cytoplasmic components from blood or to extract cytoplasmic body-free plasma, even in the absence of extraction fluid. The CBF can be effectively skimmed from the layers of the extraction channel fluid which will be relatively free of cytoplasmic bodies due to the shear-induced self-diffusion of the cytoplasmic bodies to the center of the flow. This same effect can also be used to concentrate cytoplasmic bodies in the absence of extraction fluid. Any filters (e.g., 322) at the outlets near the walls of the extraction fluid may help to inhibit and/or prevent cytoplasmic bodies from being present in the CBF taken from the extraction channel 202.

Figure 4:
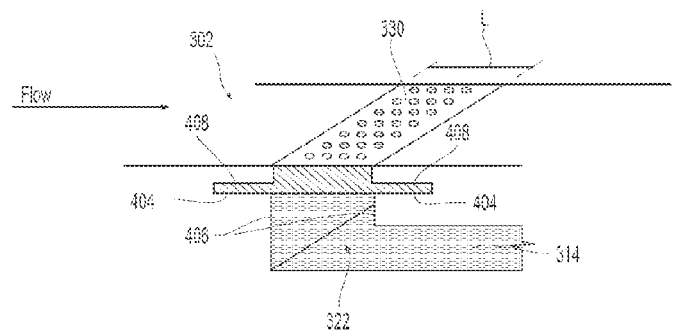
FIG. 4 is magnified isometric view of an exemplary filter employed in the membraneless separation device of FIG. 3 according to an embodiment of the disclosed subject matter.

FIG. 4 shows a close-up view of filter 330 in outlet 322 of extraction channel 302 of FIG. 3. The filter 330 can be placed in opening 322 connecting outlet channel 314 with extraction channel 302. The filter 330 can have a cross-section in the shape of an inverted "T", as shown in FIG. 4, although other cross-sectionals shapes are also possible. Opening 322 of outlet channel 314 can have two opposed grooves 404 formed in side walls 406 of opening 322. Grooves 404 can receive the two opposed tabs 408 of filter 330. This design enables filter 330 to be installed by sliding the filter 330 into place. Likewise, the filter 330 can be removed from outlet channel opening 322 by sliding the filter 330 out of the outlet channel opening 322. Such a design can allow for easy replacement of filter 330.

Filter 330 can be of such size and shape as to eliminate gaps between opening 322 and filter 330, thereby forcing the extraction fluid to flow through the pores in the surface. Alternatively, the filters can be fitted in recesses with upstream and downstream steps to support them such that a flat surface of the filter faces the extraction channel 302. Various techniques can be used to gain access to opening area 322 in order to install or remove filter 330. For example, the side of extraction channel 300 can be sealed with a removable plate. Thus, by removing the plate, one can gain access to openings 316, 318, 320, and 322. Various mechanical mounting configurations for the filters are possible including the integral formation of the filters in the materials used to create the channels 304, 306, 308, 302, 310, 312, and 314.

As shown in FIG. 4, the filter 330 can form a portion of a wall of the channel 302. The filter can define a smooth continuous surface that is coplanar with the wall of the channel 302. By doing this, the filter can remain clear of materials which may collect on the surface. This is particularly true where the channel has a small dimension in a direction normal to the surface of the filter, as is preferred, because the high shear rates of fluid resulting from the narrow space help to scour the surface of the filter. This feature is especially useful when blood is the sample fluid because proteins in the blood and cytoplasmic bodies might get stuck in a filter that does not have a relatively smooth surface. In addition, preferably, the pores define non-serpentine, non-branching channels.

Note that in a blood treatment device, filters 328 and 330 can be provided to ensure against the migration of cytoplasmic bodies into the extraction fluid outlet channels 310 and 314. Inlet filters 324 and 326 can also be provided to guard against introduction of larger particles into the extraction channel 302 and to smooth the flow of extraction fluid into the extraction channel 302. The size of the pores shown in filter 330 is greatly exaggerated for the purposes of illustration only. The actual pore size can be less than 1000 nm in diameter and preferably, 800 nm or less.

Thus, although a variety of components of the sample fluid can migrate into the extraction fluid layers while the fluids are in the extraction channel, the filters inhibit and/or prevent certain particles from leaving the extraction channel via the outlet channels. For example, if the membraneless separation device is to be used in a dialysis process to remove substances from human blood, a filter pore size of, for example, about 600 nm can be selected to exclude cytoplasmic bodies, thereby inhibiting and/or preventing the loss of cytoplasmic bodies from the blood fluid being treated, while simultaneously reducing contact between the blood fluid and the filter.

Filters can be included in openings 316 and 318 of inlet channels 304 and 308. Including filters in these openings helps to stabilize the introduction of extraction fluid by facilitating an even distribution of fluid into extraction channel 302. As with filters 328 and 300 in outlet channels 310 and 314, a shear flow across the surface of the filter is preferably maintained to sweep cytoplasmic bodies from the filter surface. The filters can be particularly useful in embodiments in which there are periods of time when there is no extraction fluid flow, but a sample fluid is flowing into extraction channel 302 via sample inlet 306. Although the pore size of a filter at the outlet and inlet may be uniform across a given filter, the pore size of an inlet filter may be different from that of an outlet filter.

The properties desired in the filters include a smooth and regular surface to permit the extraction channel flow to scour them clean and to help inhibit and/or prevent the trapping of cytoplasmic bodies or macromolecules on the surface facing the extraction channel. In addition, the channels, which can be non-serpentine and non-branching, defined in the filter can form a regular array. Also, the filters can define a smooth and direct flow path for the filtered fluid and a smooth surface facing the flow inside the extraction channel. The filter, including any support structure, can also be such that particles flow directly through the pore channels without adhering or being trapped in small surface features. The technology for creating such filters and the materials of which they are made, are numerous and it is expected that they will continue to be developed and refined. Thus, the filters are not limited to any particular method for making or structure for the filters, though the properties described are preferred for processing of blood or blood fluid.

Also, devices, methods, and systems described herein are amenable to lightweight, compact, and wearable and/or ambulatory configurations as well as configurations that can be easily administered to an ESRD patient in the home or office setting. A wearable configuration or an at-home configuration can be used as part of more frequent blood treatment sessions (as compared to conventional dialysis treatments in a hospital or clinic) in a manner that better mimics the natural functions of the human kidney. This can also improve ESRD patients' quality of life and can reduce complications, which can ultimately also reduce the mortality rate.

Figure 5:
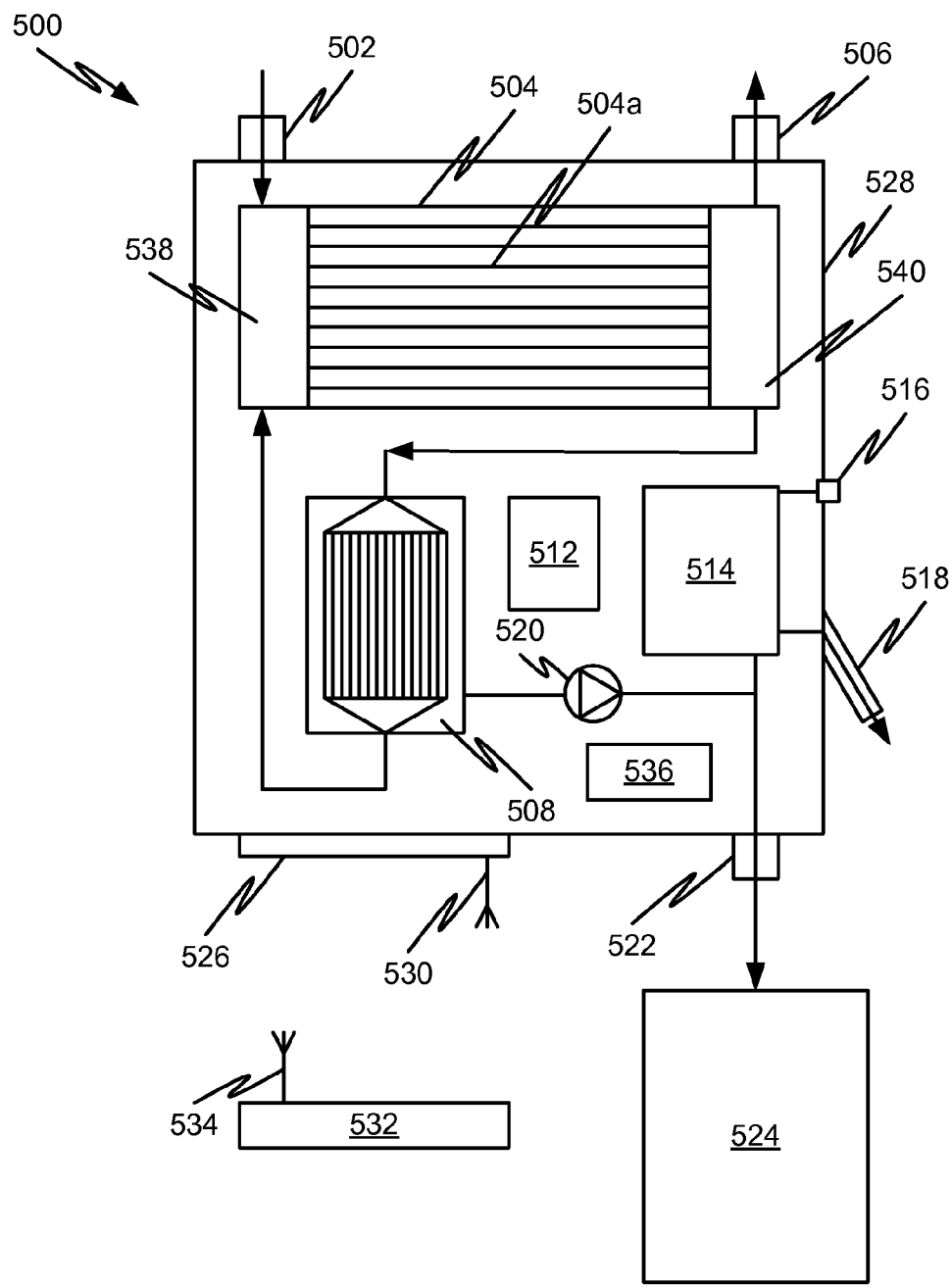
FIG. 5 is a schematic diagram of a portable ultrafiltration device using a membraneless separation device according to an embodiment of the disclosed subject matter.

FIG. 5 is a schematic diagram of a two-stage, lightweight ultrafiltration device 500 that utilizes a membraneless separation device 504 in cooperation with other treatment technologies, enabling both separation of plasma from other blood components and removal of excess fluids from blood with the objective of reducing the overall cost of delivering hemodialysis treatment, reducing the hospitalization costs associated with long-term hemodialysis, and improving the ESRD patient's quality of life. The ultrafiltration device 500 can be a portable, battery-driven unit that provides supplemental ultrafiltration and can be suitable for use by virtually all ESRD patients who currently utilize existing clinic-based and hospital-based hemodialysis machines three or more times per week.

The ultrafiltration device 500 can be configured so as to be worn by a patient, for example, on a belt around the waist, with a blood access provided by, for example, a subclavian central catheterization. The ultrafiltration device 500 may provide continuous or multi-hour extraction of excess fluid from plasma and clearance of toxins such as urea, as an adjunct therapy to conventional hemodialysis for people with ESRD. The device 500 may also reduce the necessity for clinic or hospital based hemodialysis by 33-66% by supplementing conventional renal replacement therapy treatments. The continuous daily use of ultrafiltration may help to stabilize the excess fluid levels of patients and reduce the frequency of conventional treatments required, potentially improving quality of life for ESRD patients and potentially providing cost benefits. The portable ultrafiltration device described herein allows the patient to move about in a normal manner (e.g., go to work, school, home, etc.) while being subject to ongoing dialysis.

The ultrafiltration device 500 as described herein can be wearable on a long-term, continuous basis (e.g., 10 to 196 hours) and can be designed to provide ultrafiltration of excess fluid (e.g., 25-75%) that arises from an ESRD patient's inability to urinate, as well as provide clearance of a portion (e.g., 10-25%) of toxins required to be removed per week. Such a device can reduce the need from the typical three visits per week for dialysis in a clinic or hospital setting, where over 90% of the hemodialysis patient population currently receives treatment.

Cost-saving improvements afforded by the ultrafiltration device 500 can include reduced labor costs by virtue of fewer weekly dialysis treatments at a dialysis center (e.g., clinic or hospital setting) as a result of the increased efficiency in removing excess fluid and toxins on a continuous basis during the times when the ESRD patient is not receiving dialysis treatment at a dialysis center and a reduction and/or elimination of the need for dialysate and the associated substantial issues of liquid handling which it gives rise to. This brings a long-term benefit of the membraneless separation device (e.g., no contact between the blood and an artificial surface during the dialysis process) to a much wider range of ESRD patients with concurrent positive impacts on overall hemodialysis and hospitalization costs.

The ultrafiltration device 500 can employ a membraneless separation device 504 having multiple membraneless extraction channels 504a arrayed in the exchanger and a membrane, such as a dialyzer 508, that does not use dialysate or uses a relatively small amount of dialysate either intermittently or continuously at a much lower rate than conventional dialysis such that substantial quantities of exogenous fluids need not be carried by the patient. Blood (or other sample fluids) from the patient enters the device 500 through blood inlet 502 into the first stage module 504, which contains the membraneless extraction channels 504a linked together by distribution and collection manifolds 538 and 540. Distribution manifold 538 distributes fluid to each membraneless extraction channel 504a while collection manifold 540 collects the fluid from each membraneless extraction channel 504a. Blood returns to the patient through blood outlet 506.

The membraneless extraction channels 504a are described in more detail with reference to FIG. 1A above. Separation of plasma from blood, as well as diffusion of metabolic toxins from the ESRD patient's blood into a surrounding extraction fluid occurs within the membraneless separation device 504. The flow of blood through the membraneless separation device 504 is driven by one or more pumps (not shown). The rate of flow and dimensions of the channels 504a are such that plasma may be separated from the cytoplasmic bodies and removed through a plasma separation process inherent in the membraneless separation device as described throughout the present disclosure. The membraneless separation device 504 can be replaced at regular intervals or reused after cleaning and sterilization.

The membraneless separation device 504 can be coupled to a second stage small, replaceable unit 508, which may have a bundle of hollow filter fibers such as used in common dialyzers. The second stage 508 receives only plasma separated by the membraneless separation device 504. The area of the membrane is preferably suitable for a prescribed function. For example, the membrane area may be about 200-3,000 $cm^2$ for the principal application described herein of ultrafiltration.

A pressure differential can be created by a pump 520 to remove a desired volume of fluid, which includes toxins and other non-cytoplasmic components. The second stage treatment device 508 selectively permits the removal of fluid and unwanted components, e.g., ionic species and undesired middle molecules, while retaining macromolecules and other particles desired to be returned to the blood. Preferably, no dialysate is used in the second stage 508. The excess fluid, which also contains metabolic toxins, flows along a path to a waste port 522 and a waste receptacle 524, for example a 1-41 collection bag, attached thereto. The waste receptacle can be worn and periodically emptied by the patient, similar to a colostomy bag. The waste port 522 can be provided with an attachment mechanism, such as a clip, for releasably attaching the waste receptacle thereto.

Alternatively, or additionally, the ultrafiltration device 500 can be provided with an onboard reservoir 514 for receiving and storing excess fluid, which also contains metabolic toxins, for disposal. For example, the onboard reservoir 514 can have a volume of 400-500 ml. At an ultrafiltration rate of 125 ml/hour, the onboard reservoir 514 would thus need to be emptied every 3-4 hours and would be comparable, in terms of fluid volume capacity, to a normal bladder. The housing 528 can include a drop-down spout 518, which would enable the patient to empty the reservoir 514 when full. The housing 528 can also have an air valve 516 to allow air to vent out of the reservoir 514 when the reservoir is being filled or emptied.

Sensors can be provided for monitoring the reservoir 514, a status of the emptying mechanism, and a connection status of a waste receptacle to the attachment mechanism. For example, a sensor can be provided on the spout 518 to detect that it is in the closed (e.g., up) position. A sensor on the waste port can detect if a waste receptacle is attached. A sensor on the reservoir 514 can detect when the reservoir is full. In the event of any of any conditions requiring it, such as the spout being down, the reservoir being full, or other scenarios requiring immediate intervention, the patient can be notified via audible or visual mechanisms.

The reduced fluid can be returned to membraneless exchanger 504 via manifold 538 so as to normalize with the blood flood therein and thus return it to the body, resulting in ultrafiltration. A pump can drive the return of the extraction fluid (e.g., water and uremic toxin-depleted plasma) back to the first stage membraneless separation device 504, so as to provide for continuous flow, with the resultant plasma separation, ultrafiltration of excess fluids, and clearance of metabolic toxins.

The small pump 520 can be used to create the partial vacuum necessary to extract a measured quantity of excess fluid from the second stage 508. A programmable electronic module 512 can control the device 500 and provide safety shutoff. A power supply 536, for example, a replaceable or rechargeable battery pack, can be incorporated in the housing 528 to provide power to various components of the ultrafiltration device 500.

Prior to operation, the membraneless exchange device 504 and the other fluid components of the ultrafiltration device 500 can be primed with a blood normal solution, such as saline. Thus, the initial extraction fluid circulating in the membraneless exchange device 504 would be the blood normal solution. However, within a short time after starting operation, the extraction fluid equilibrates with, and is eventually replaced by, plasma flowing through the first stage 504 and the second stage 508. Provision can also be made for a reservoir of blood normal solution (not shown), either with the housing or elsewhere, which would be periodically consumed automatically in the housing 528 during startup or to flush any filters in the first stage 504.

The ultrafiltration device 500 can be housed in a compact enclosure 528 (e.g., 3 to 20 in$^3$, or similar to the dimensions and weight of an ambulatory infusion pump device) attached to the patient (e.g., strapped to the patient's forearm, leg or abdomen, or worn externally on a belt, sling, or backpack) and connected to one or two shunts, catheters or other conventional circulatory system ports (one for blood flowing out from the ESRD patient, the other for blood flowing into the ESRD patient), having one or more lumens, that are inserted in a convenient spot (e.g., the arm, or leg or torso or abdomen), which can supply a blood flow of 20-120 ml/minute through tubing (e.g., silicone tubing) to the enclosure. The ultrafiltration device 500 can either be attached, removed and serviced at regular intervals by a technician at a clinic, or made disconnectable and reattachable from/to the patient, without the need for a technician to reinsert needles into the patient's venous system (e.g., using a catheter or subcutaneous ports already in use for parenteral nutrition or other blood access devices such as infusion systems).

The housing 528 can also be provided with an external input/output device or interface 526. The interface 526 can communicate with controller 512 to provide instructions thereto or for programming the controller 512. Moreover, the interface 526 may provide data or alarm signals to a patient or operator through visual and/or auditory mechanisms. For example, if the controller 512 detects an alarm condition, the patient can be alerted to seek medical attention by a flashing light and/or a siren from interface 526. In addition, the interface 526 can be used by the patient to adjust, pause, stop, and/or restart ultrafiltration. For example, the patient can pause the ultrafiltration by touching an appropriate control on the interface 526.

A variety of sensors can be provided throughout the ultrafiltration device 500 to monitor the condition of the blood flowing to the patient as well as to monitor effective operation of the ultrafiltration device. For example, a sensor can be provided inline with blood flowing to the patient between blood outlet port 506 and manifold 540 so as to monitor characteristics of the blood flowing to the patient. Such sensors can include, but are not limited to, a hematocrit sensor, electrolyte sensor, a glucose monitor, or a potassium sensor. The transmembrane pressure (TMP) of the second stage 508 can also be monitored via an appropriate sensor to provide an alarm in the event of membrane failure.

A variety of blood monitoring sensors can also be integrated into the ultrafiltration device 500 to track blood components. Data from the sensors can be stored on-board with the ultrafiltration device in a memory device (not shown). Such a memory device can be incorporated with controller 512 or provided separately within housing 528. Data can be sampled from the sensors in real-time, periodically, or coincident with certain events that may impact blood treatment. The data can be used by the controller 512 for on-the-fly control and optimization of the ultrafiltration or for periodic updates to the ultrafiltration regimen.

The data can be used to monitor blood conditions for safety purposes, for example, to inhibit and/or prevent hypervolemia or hypovolemia. Stored data can also be transmitted to a doctor for review, for example, as the basis for prescription and/or diet/lifestyle changes. Moreover, the data can be used for research purposes. For example, the stored data can be used to correlate health events, such as a heart attack, to real-time changes in blood properties. The results of these studies can then be used by the controller 512 to monitor data trends that can signal an imminent health event.

Input/output interface 526 can also be provided with a communication mechanism for communicating with other monitoring and/or treatment devices so as to transmit or receive data and/or instructions. For example, the interface 526 can be provided with an antenna 530 configured to communicate with a device 532, which also can have an antenna 534 for wireless communication between the two devices. Alternatively, instead of the wireless communication setup illustrated in FIG. 5, interface 526 can directly be connected via a wire or cable to device 532. Device 532 can be another health monitoring system provided on or in a patient. For example, the device 532 can be a heart monitor associated with an implanted pacemaker, defibrillator, or a standalone implanted hemodynamic monitor. Device 532 and interface 526 can share data as appropriate so as to provide a unified treatment system. Thus, the ultrafiltration device can be part of an automated system that interacts with other medical devices (e.g., a pacemaker, defibrillator or heart monitor) to control the devices and potentially allow unique interventions, for example, injection of appropriate medicaments and cessation of ultrafiltration due to sudden drop in blood pressure.

The regulation of the flow to the first and second stages can be provided by any suitable means, such as valves, flow diverters, gates, switches, pumps and can include the use of bypass flows, among the various sets of multiple arrays in the membraneless separation device 504. A technician can program the sequence and timing for the given flow levels by entering data into control module 512 or the program can be entered or selected by other means. The flow control components can be actuated, for example, by gang actuators, by micro-electromechanical machines (MEMS) actuators, or by any suitable means.

Since the ultrafiltration device 500 can provide extended treatment times due to its low extracorporeal blood volume, it is therefore possible to provide the ultrafiltration device in a compact configuration. For example, a wearable (or at least portable) system according to the present disclosure can run between 20 and 24 hours per day at a blood flow rate of about 20-50 ml/min, for example. The patient can then have, for example, 4-5 hours each day without the device in place which can be used for personal hygiene (e.g., showers or baths), sports activities, or other activities not amenable to the small system being worn or used.

In another example, the resulting ultrafiltration rate from use of the ultrafiltration device can be between 100 and 300 mL/hr, for example, 125 mL/hr. With such an ultrafiltration rate, the vast majority of patients will be able to fulfill their daily ultrafiltration prescription during the normal waking hours. High volume patients would receive nocturnal ultrafiltration with the ultrafiltration device by simply connecting a waste receptacle to the waste port of the housing before they go to sleep.

The ultrafiltration device 500 can be configured to permit selection among various flow rates and/or to vary flow rate automatically according to a treatment regimen. The membraneless separation device 504 with arrays of microfluidic channels 504a can use all, or various subsets, of the channels depending on a given ESRD patient's needs in order to maintain specified ranges of flow rates in each channel. For example, a prescribing doctor or selected treatment protocol may require a high flow rate for one portion of the treatment and a lower flow rate for the balance.

In a variation, the ultrafiltration device can operate to remove excess fluid from a patient suffering from congestive heart failure. In another variation, the ultrafiltration device can operate to remove excess fluid from a patient suffering from pulmonary edema. In yet another variation, the ultrafiltration device can operate to remove excess fluid or toxins from a patient suffering from various diseases of the liver, including high cholesterol levels.

Figure 6:
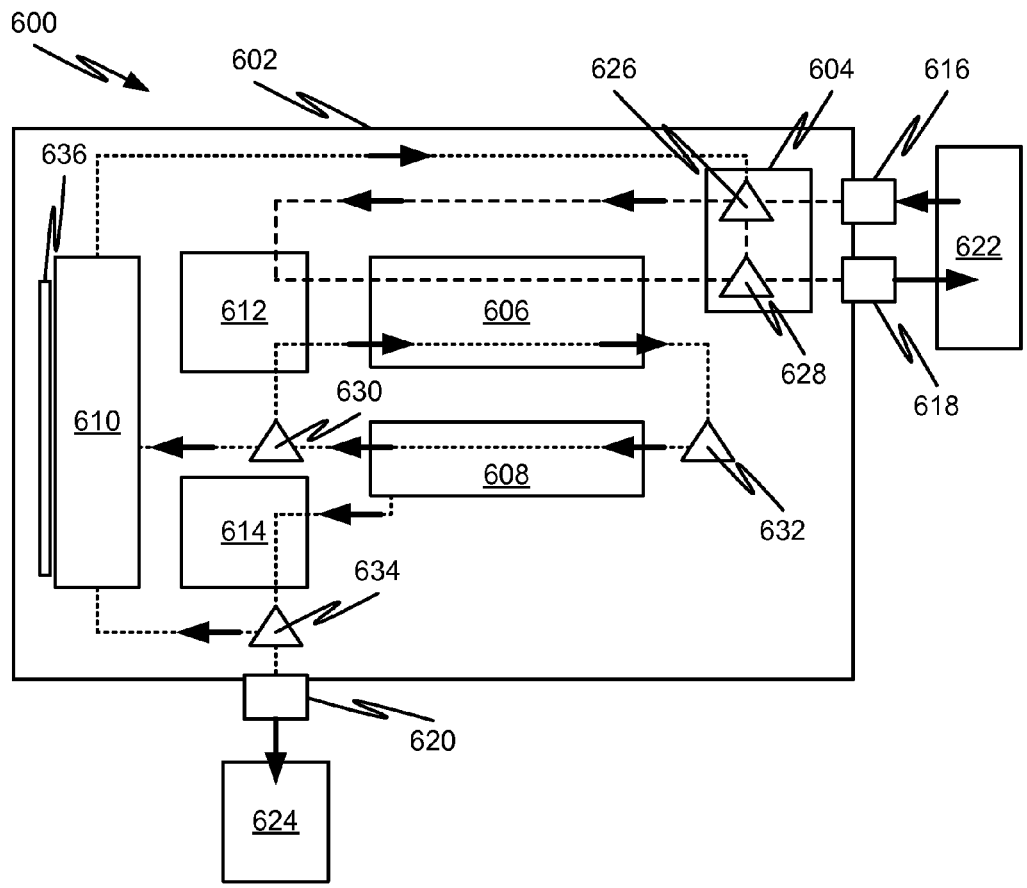
FIG. 6 is a schematic diagram of an ultrafiltration device using a membraneless separation device according to an embodiment of the disclosed subject matter.

FIG. 6 illustrates a detailed schematic of the flowpaths employed in an ultrafiltration device. A patient 622 can be attached to the ultrafiltration device 600 via blood inlet port 616 and blood outlet port 618. A bypass module 604 can be operatively connected to both ports. Blood inlet valve 626 in the bypass module 604 can be connected to inlet port 616 while blood outlet valve 628 can be connected to outlet port 618. The valves 626 and 628 can be configured such that blood entering blood inlet port 616 can be shunted to blood outlet port 618 by appropriate selection of the valve states.

Pump 612 can flow fluid from valve 626 through the membraneless separation module 606 and to valve 628 for return to a patient. Pump 612 can also serve to flow the extraction fluid through membraneless separation module 606 to secondary processor by way of a first extraction fluid valve 632. A second extraction fluid 630 can be arranged between the outlet of the secondary processor, a holding tank 610, and the extraction fluid inlet of the membraneless separation module 606.

Waste from the secondary processor 608 can be directed by ultrafiltration pump 614 to valve 634. By appropriate selection of the state of the valve 634, the waste can be directed to either hold tank 610 or waste port 620. At waste port 620, a waste receptacle 624 can be arranged to collect the waste. Holding tank 610 can have an outlet connected to the blood inlet valve 626. The holding tank 610 can also have a heater 636 arranged adjacent thereto or disposed internal to the holding tank for heating the contents thereof.

In a fill and priming sequence of the ultrafiltration device 600 prior to use by a patient, a bag with a blood normal priming fluid, for example, saline, can be connected to blood inlet port 616. Both the blood inlet valve 626 and the blood outlet valves 628 can be opened. Pump 612 can then be turned on so as to circulate the priming fluid until the priming fluid passes valve 628 and all air has exited the blood circuit (dashed lines) via the blood outlet port 618. At this point, the blood outlet valve 628 can be closed and extraction fluid valves 632 and 630 can be opened. The pump 612 can continue to circulate the priming fluid until the sheath circuit (dotted lines), secondary processor, and holding tank are full and all air has exited through the air purge at port 616. At this point, the pump 612 can be turned off and blood inlet valve 626 and blood outlet valve 628 can be closed. This assumes that the priming fluid would pass through any filters in the membraneless separation device 606 so as to fill the secondary processor 608.

When the ultrafiltration device has completed its treatment of a patient for a given period, the device can be shut down and removed. However, if blood is not cleared from the device, the blood may coagulate within the channels of the membraneless separation device, thereby preventing its reuse. Accordingly, the ultrafiltration device 600 can employ a shutdown sequence to ensure that all blood is cleared from the system.

To shut down the ultrafiltration device 600, blood inlet valve 626 can be closed, and ultrafiltration pump 614 can be turned on. Valve 634 can then be closed. The blood inlet valve 626 can be switched from the blood inlet port 616 as the source to the outlet of the holding tank 610. Diversion of the ultrafiltrate to the holding tank 610 can be designed to circulate fluid through the blood circuit portion (dashed lines) of the membraneless separation device 606. Once the blood circuit is full of fluid from the holding tank 610, all valves and ports can be closed and all pumps can be shut off. The point at which the blood circuit is full can be determined through experimentation or by using an appropriate sensor arranged in the blood circuit.

For subsequent reuse by a patient, the ultrafiltration device can undergo a sterilization procedure. For example, blood inlet port 616 and blood outlet port 618 can be closed and the bypass between blood inlet valve 626 and blood outlet valve 628 can be opened. Valve 630 can be opened to the holding tank. The ultrafiltrate pump 614 can be maintained in an off state during this time. The holding tank heater 636 can be turned on so as warm the fluid therein to an elevated temperature, for example, about 60 to 85° C. Once this temperature is reached, pump 612 can be activated to circulate the heated fluid from the holding tank through the blood circuit (dashed line) and the sheath circuit (dotted line) as well as the secondary processor for an extended period of time, for example, about 1 to 4 hours. The priming fluid can then be drained from the ultrafiltration device at the end of the sterilizing sequence.

Alternatively, the priming fluid can be reused. Valve 634 can be used to shunt ultrafiltrate into the holding tank to fill it up as needed.

The secondary processor 608 may require periodic replacement due to device failure or use of the ultrafiltration device 600 in a different treatment modality. Assuming the ultrafiltration device 600 is already shutdown, valves 630 and 632 can be closed. The old secondary processor can then be manually removed and a new secondary processor inserted. The fill and priming sequence described above can then be repeated.

A problem with existing treatment technologies is that they ultrafiltrate at a rate well in excess of the body's natural fluid flow (400 ml/hr) from cells and extracellular space to the blood stream. Consequently, the patient suffers from rapid fluid swings, low blood pressure, nausea, fainting, excessive time for recovery post dialysis, etc. Therefore, performing hemodialysis, hemofiltration, or hemodiafiltration typically results in an ultrafiltration rate that is beyond the physiologic limit for fluid transfer which can lead to complications. To remedy this, it is contemplated that hemofiltration, hemodialysis, or hemodiafiltration can be performed at a reduced frequency to reduce and/or minimize the complications associated with the hemodialysis, hemofiltration, or hemodiafiltration treatments, while providing effective, longer treatment period ultrafiltration at a lower flow rate. Thus, the ultrafiltration device employing the membraneless exchange, as described herein, can be used as part of a comprehensive treatment protocol for patient lifestyle amelioration. The ultrafiltration employing the membraneless exchange, with or without anti-coagulants, may be performed using a portable device, as described above with reference to FIG. 5, or as a standalone treatment in a clinical setting. Alternatively, the ultrafiltration employing the membraneless exchange can be performed sequentially together with conventional dialysis treatments in a clinical setting.

Figure 7:
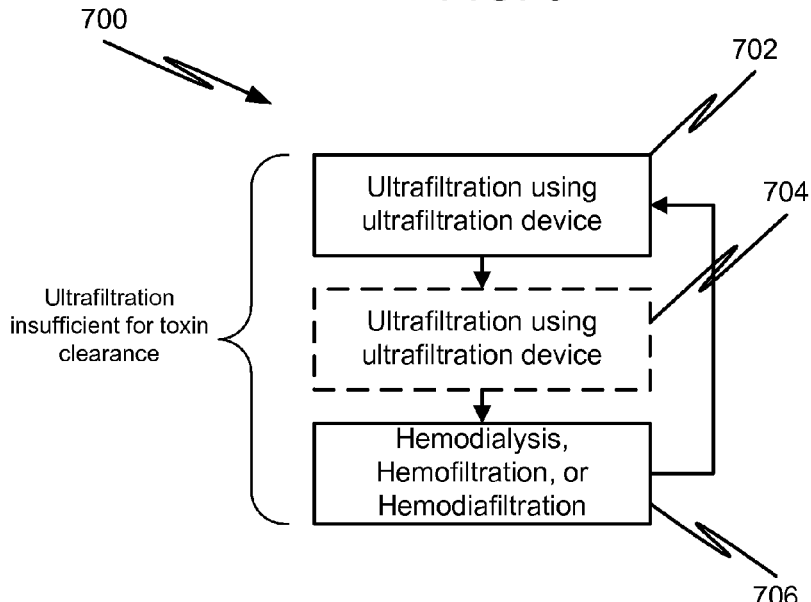
FIG. 7 is a flowchart illustrating a dialysis treatment regimen according to an embodiment of the disclosed subject matter.

For example, FIG. 7 illustrates a dialysis treatment regimen 700 incorporating multiple ultrafiltration sessions. In particular, multiple ultrafiltration sessions 702, 704 (of which, secondary ultrafiltration session 704 may be optional) are performed in conjunction with conventional therapies 706, such as, but not limited to hemofiltration, hemodialysis, hemodiafiltration, hemosorption, and other treatments described herein.

In FIG. 7, ultrafiltration sessions 702 and/or 704, preferably but not necessarily performed by a portable device, can be performed at a higher frequency and for longer periods overall than conventional treatment. This is done such that the fluid burden can be managed by long term, low rate, regular (e.g. daily or every other day) treatment and supplemental toxin clearance can be managed by less frequent sessions of conventional therapy. The ultrafiltration sessions 702 and/or 704 can be performed according to the embodiments of FIGS. 2A-2B. For example, the ultrafiltration sessions 702 and/or 704 may employ the arrangement shown in FIG. 2B, wherein the secondary processor 236 includes an ultrafilter. In another example, the ultrafiltration sessions 702 and/or 704 may employ the arrangement shown in FIG. 2B, wherein the secondary processor 236 includes a sorption device for sorbent-based blood toxin removal. The sorption device can be configured to remove at least urea from the CBF from a membraneless separation device by passing the CBF across a sorbent. In still another example, the ultrafiltration sessions 702 and/or 704 may employ the arrangement shown in FIG. 2B, wherein the secondary processor 236 includes at least one of an ultrafilter and a sorption device.

A complementary use of ultrafiltration, either ambulatory, at home, or in a clinical setting, in conjunction with conventional treatment normally provided in a clinic can have a tremendous impact on patient health and lifestyle. The ultrafiltration treatment can be performed with an ultrafiltration device, as discussed herein. Moreover, the ultrafiltration device can be configured to be easily set up by the technician at the dialysis clinic after conventional treatment, or by patients or minimally trained caregivers at the home or office of the patient. The ultrafiltration device may operate at blood flow rates, for example, less than 1 ml/sec for periods of at least 6 hours per day, preferably at least 8 hours per day, more preferably at least 12 hours per day, and even more preferably for lengthy durations (e.g., 4 to 8 hours), and for some patients approaching continuous use except for breaks of not more than 4 hours total. The ultrafiltration device (e.g., as shown in FIG. 2A or 2B) can also be used at least nocturnally. The ultrafiltration device as part of the treatment protocol 700 in FIG. 7 operates to remove water from the blood at a rate of no more than about 0.4 l/hr and preferably, substantially less. The blood flow rate during the ultrafiltration session 702 and/or 704 can be between 0.5 ml/second and 5 ml/second.

The ultrafiltration device can be used daily in conjunction with a direct toxin-removing therapy according to any of the descriptions of complementary therapy described below. As previously described, the ultrafiltration device can preferably, but not necessarily, employ a sheathed flow of blood in a membraneless separation device to reduce and/or minimize contact of blood with artificial surfaces that cause negative biocompatibility reactions. Moreover, the sheathed flow, if used, can be established in a membraneless separation device employing channels with channel filters such as indicated 330 in FIG. 4 and preferably employ flow conditions as described herein, especially such conditions as required for clearing cytoplasmic bodies from channel filters.

The ultrafiltration device can be portable and preferably can be worn by the patient. Such a portable device can be configured to require no external power connection by being battery powered. The ultrafiltration device can require substantially no dialysate or consumable fluids, other than what may be required for initial priming and filling before use. The ultrafiltration device can also include an onboard waste collection reservoir or a waste collection receptacle, such as a collection bag, that can be worn by the patient.

Any or all of the enumerated features of the treatment protocol 700 of FIG. 7 and the disclosed ultrafiltration device may be employed in any combination to provide an effective patient treatment. For example, a method of treatment can include ultrafiltration (ambulatory, at home, or in a clinic) on a daily basis supplemented by conventional treatment at a frequency that is greater than daily, and preferably two days per week. The ultrafiltration can be done using a portable device, whether a membraneless exchanger or not. The ultrafiltration can be done in a way that uses a membraneless exchanger to limit the exposure of whole blood to filter membranes.

Additional variations can include performing daily ultrafiltration using a portable ultrafiltration device supplemented by sorption-based dialytic treatment using a portable sorption-based dialyzer every other day or performing daily ultrafiltration using a portable ultrafiltration device and supplemented by sorption-based dialytic treatment using a portable sorption-based dialyzer every other day supplemented by conventional dialysis using fresh dialysate once or twice per week.

The ultrafiltration device can also be used daily in a treatment method that includes direct toxin-removing renal replacement therapy (conventional therapy) no more than twice a week. The conventional therapy can include at least one of hemofiltration, hemodialysis, and hemodiafiltration. At least, the method can include performing ultrafiltration interspersed with conventional therapy, for example, ultrafiltration being performed daily and convention therapy being performed once or twice per week. The method can include performing ultrafiltration for longer periods at lower flow rates than conventional therapy. In addition, the method can include performing ultrafiltration more frequently than conventional therapy. At least the ultrafiltration portion of the treatment method can employ a membraneless exchange device.

While primarily discussed above with regard to the ultrafiltration of blood, the membraneless separation device is applicable to a range of extracorporeal biological fluid processing. For example, the membraneless separation device can be used to create a CBF from flowing blood that can be analyzed. The analysis can occur in real-time by using an in-line analysis system. Alternatively, or additionally, the cytoplasmic body-enriched fluid fraction of the flowing blood can be analyzed or sampled. Because of the relatively small sample volumes enabled by the microfluidic dimensions of the membraneless separation device, minimal patient impact is expected, thereby enabling the membraneless separation device to be incorporated in a wearable device for continuous fluid monitoring.

Figure 8:
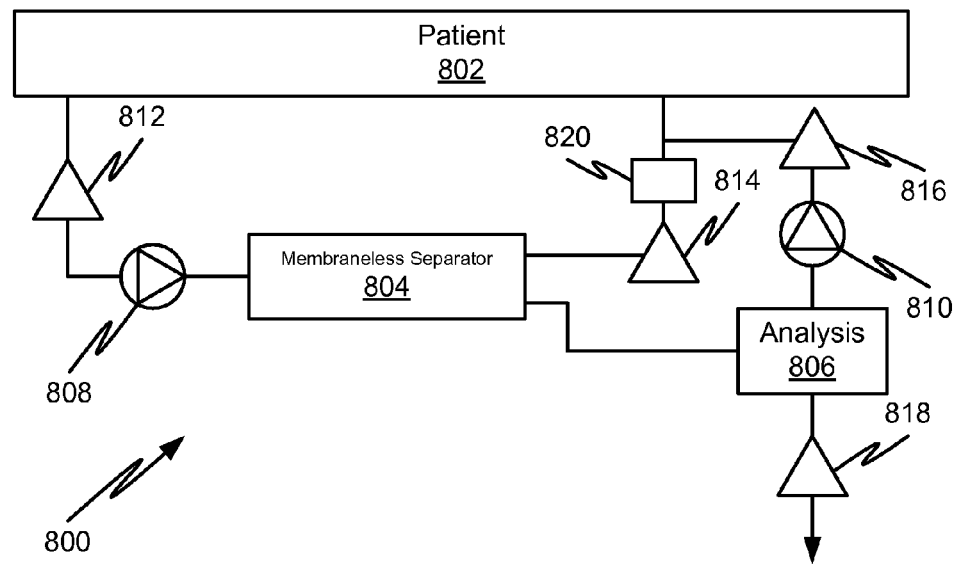
FIG. 8 is a schematic diagram of a fluid fraction analysis system employing a membraneless separation device and an analysis system according to an embodiment of the disclosed subject matter.

A fluid fraction analysis system 800 incorporating a membraneless separation device 804 and an inline analysis system 806 is shown in FIG. 8. For example, the fluid fraction analysis system 800 can be configured as a blood plasma analysis device. Thus, plasma can be withdrawn from a small separation channel (preferably conforming to the height and width specifications described elsewhere herein). Blood from a patient 802 can be continuously drawn by means of a pump 808. Plasma can be separated from blood in the separation channel 804 by the same mechanisms as described above, including the use of channel filters.

The substantially cytoplasmic body-free plasma fraction can be sent to the analysis system 806 for analysis while the remaining blood fraction can be returned to the patient 802 by way of valve 814. An optional blood monitoring sensor 820 can be disposed between the blood outlet of the membrane separation device 804 and the patient 802 to monitor the blood for potential safety issues, such as device failure or blood clots. Note that pump 808 can be configured to flow the blood from the patient through the membraneless separation device 804. Although the pump 808 is shown upstream from the separation device 804, the pump can be arranged at other positions within the flow path. Moreover, additional pumps can be used. Also, no pumps can be used. In such a pumpless configuration, the blood flow through the membraneless separation device would rely on blood pressure from the patient 802. Thus, the membraneless separation device 804 can be configured to generate a predefined plasma flow rate to analysis system 806 based on blood pressure or using a pump 808.

Connected to the plasma outlet can be a continuous analyzer 806. Here, the system 800 can be used such there is only a very short delay between the point in time when the plasma is traveling with blood in the patient 802 and the point in time where it is analyzed by analyzer 806. The analysis system 806 can have a flow channel configured such that no stagnant flow regions exist under the predefined plasma flow rate such that it is continuously purged by incoming plasma. In this way, near real time measurements of a blood component can be made. Examples of continuous analyzers include, but are not limited to, spectrophotometers, conductivity sensors, and pH sensors.

Cytoplasmic body-free plasma from the analysis system 806 can be returned to the body along with blood flow from the membraneless separation device using plasma pump 810 and valve 816. Alternatively, the analyzed cytoplasmic body-free plasma can be disposed of by opening valve 818. Similarly, even though the blood is shown in FIG. 8 as being returned to the patient 802, the cytoplasmic body-enriched component can be disposed of or returned to the patient. The plasma or cytoplasmic body-enriched component can be conveyed to an analyzer 806, which can be a single use or a continuous analyzer. In a system in which a continuous analyzer is used, the plasma, for example, can be continuously extracted at a low rate, for example, less than 0.5 ml/min. This can be done during a treatment and thereby permit continuous analysis of blood components otherwise made difficult by a requirement of separation or concentration of cytoplasmic components. For example, an optical technology such as an absorption spectrometer can be used to analyze the plasma stream continuously.

Figure 9:
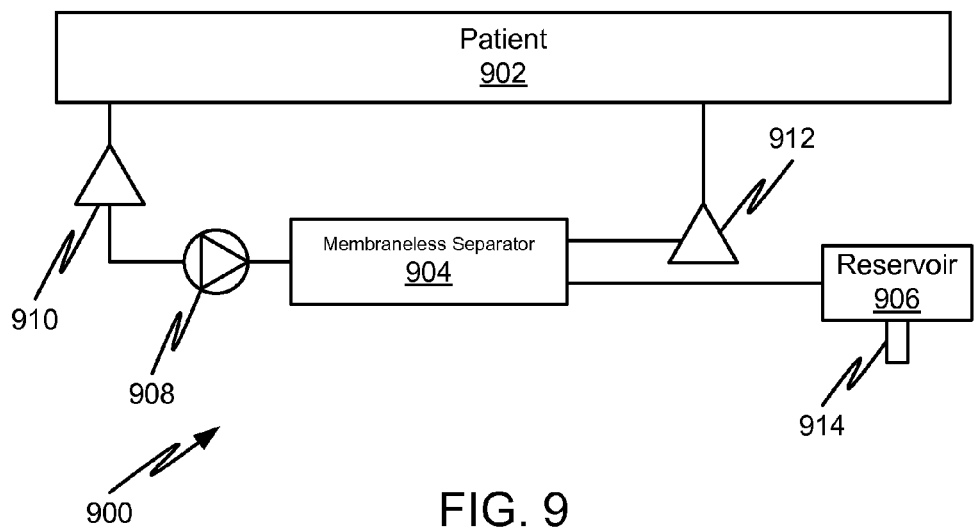
FIG. 9 is a schematic diagram of a fluid fraction analysis system employing a membraneless separation device and a reservoir according to an embodiment of the disclosed subject matter.

Alternatively, as shown in FIG. 9, a sample reservoir 906 can be connected to the plasma outlet of a membraneless separation device 904. Such a system 900 receives blood from a patient 902 and uses a pump 908 to flow the blood through the membraneless separation device so as to produce a cytoplasmic body-free plasma fraction and a cytoplasmic body-enriched blood fraction. The cytoplasmic body-enriched blood fraction can be returned to the patient 902 via valve 912. The reservoir 906 can serve to capture the plasma from the patient 902 for subsequent treatment, analysis, transfusion, medicament, or manufacturing purposes. The reservoir 906 can include a needle port 914 to enable intermittent manual sampling by a user.

In yet another alternative, the outlet of the membraneless separation device 904 can be connected to nothing at all. In such a configuration, for example, a test strip or analysis solution can be periodically contacted with the cytoplasmic body-free plasma exiting the membraneless separation device outlet so as to make a measurement.

The cytoplasmic body-free fraction analysis can operate to reduce and/or minimize the amount of plasma sampled and thus the amount of plasma lost in the analysis. Such a configuration can enable the analysis system to be miniaturized and potentially to be worn continuously while reducing and/or minimizing plasma loss by the patient. Alternatively, the device can be configured to provide a plasma fraction at intervals. This can be achieved by manipulating the flow rate in the membraneless separation device by controlling pumps. For example, the pumps can be turned on and off at intervals. The pump speed can also be controlled to control the sampling rate, such as switching between slow and fast speeds.

Because the analysis system can be connected to a patient continuously, backflow from the membraneless contactor to the patient should be prevented during intermittent analysis or in the event of pump failure. This can be achieved by providing a safety valve (812, 910) between the patient and the membraneless separation device (804, 904). The safety valve can take the form of an inline clamping valve or an inline check valve.

In any event, it is desirable to minimize the total volume taken from the patient. By providing the device in close proximity to the patient, path length can be reduced and/or minimized and thus the overall amount of fluid necessary to fill the analysis device can also be reduced and/or minimized. The small size of the membraneless contactor also results in a low sample volume. The location of pumps and valves in the analysis device can also be arranged to reduce and/or minimize the volume of fluid from the patient necessary for analysis.

Figure 10:
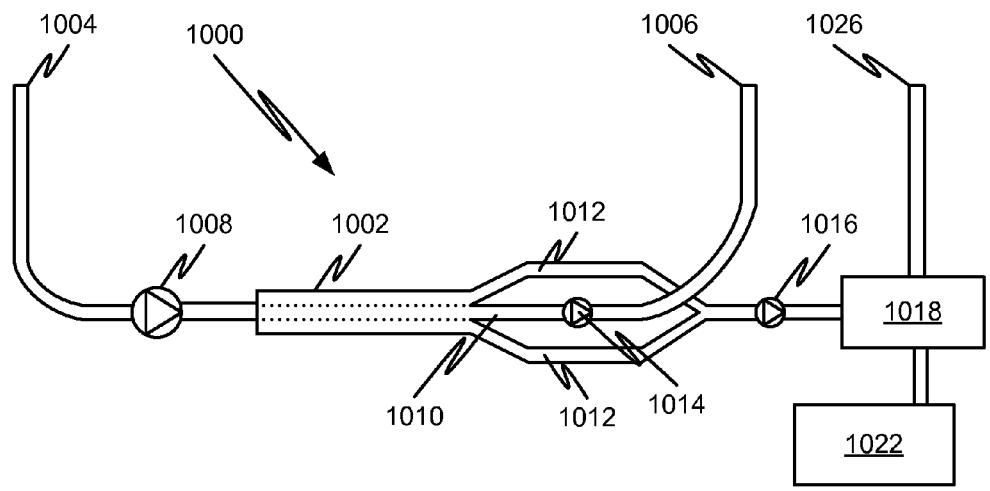
FIG. 10 is a schematic diagram of a fluid fraction extraction system employing a membraneless separation device according to an embodiment of the disclosed subject matter.

Since the membraneless separation device is fully capable of extracting plasma, as discussed herein, the membraneless separation device can be used to remove plasma which may be treated or replaced with fresh plasma or other fluid without the need for centrifuging blood. FIG. 10 illustrates a plasma treatment device 1000 employing a membraneless separation device. In particular, the membraneless separation device can have an extraction channel 1002 with a blood outlet channel 1010 and plasma outlet channels 1012. A blood inlet pump 1008 can convey whole blood from an access 1004 connected to a patient (not shown). A blood outlet pump 1014 can convey cytoplasmic body-enriched blood received in blood outlet channel 1010 back to the patient through access 1006. The cytoplasmic body-free plasma streams in outlets 1012 can be conveyed to a treatment module 1018 via pump 1016. As previously described, the flow rates of pumps 1008, 1014 and 1016 can be controlled to insure a substantially cytoplasmic body-free plasma fraction in outlet channels 1012. Moreover, the outlet channels 1012 can be provided with channel filters, as previously described, to inhibit and/or prevent the migration of cytoplasmic bodies into the outgoing plasma fraction.

The treatment module 1018 can perform a blood treatment, such as a dialysis treatment, provide a medicament to the cytoplasmic body-free plasma fraction, or perform any other treatment of plasma known in the art. After treatment by the treatment module 1018, the plasma can be directly infused to the patient via access 1026. Alternatively, the treated plasma can be stored in a receptacle 1022 for later infusion into the same patient or a different patient, for example, in a plasma transfusion.

Figure 11:
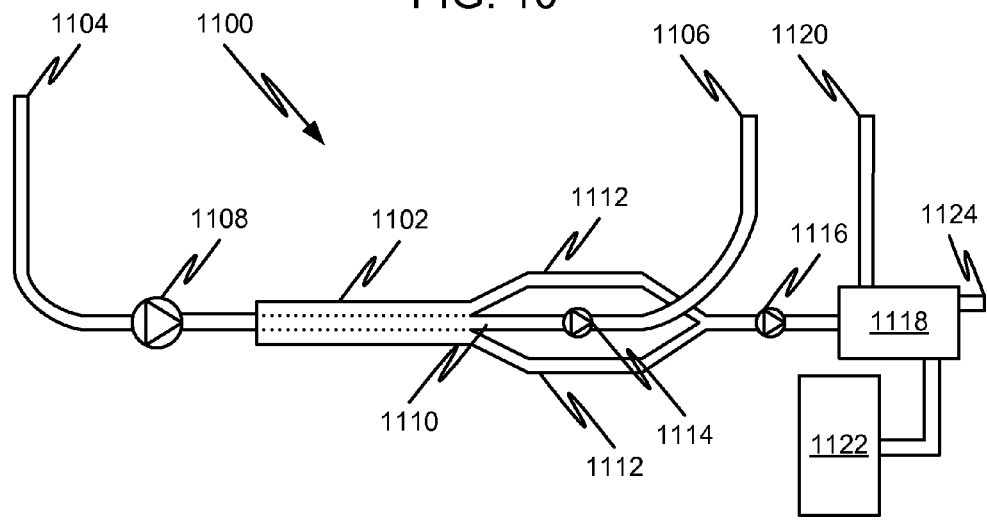
FIG. 11 is a schematic diagram of a fluid fraction replacement system employing a membraneless separation device according to an embodiment of the disclosed subject matter.

In therapeutic apheresis for total plasma exchange, the membraneless separation device would replace the centrifuge currently used in conventional blood/plasma separation technologies. Because of the reduced contact with artificial surfaces afforded by the membraneless separation device, there is a reduced or eliminated need for anti-coagulants. Moreover, the membraneless separation device can operate with a much smaller extracorporeal volume. Embodiments may therefore be suitable for pediatric cases to which systems requiring larger volumes cannot be applied. FIG. 11 illustrates a therapeutic apheresis device 1100 incorporating a membraneless separation device.

In particular, the membraneless separation device can have an extraction channel 1102 with a blood outlet channel 1110 and plasma outlet channels 1112. A blood inlet pump 1108 can convey whole blood from an access 1104 connected to a patient (not shown). A blood outlet pump 1114 can convey cytoplasmic body-enriched blood received in blood outlet channel 1110 back to the patient through access 1106. The cytoplasmic body-free plasma streams in outlets 1112 can be conveyed to a plasma exchange device 1118 via pump 1116. As previously described, the flow rates of pumps 1108, 1114 and 1116 can be controlled to insure a substantially cytoplasmic body-free plasma fraction in outlet channels 1112. Moreover, the outlet channels 1112 can be provided with channel filters, as previously described, to inhibit and/or prevent the migration of cytoplasmic bodies into the outgoing plasma fraction.

The plasma exchange device 1118 can employ a flow regulator and a balancing device that ensures a desired plasma balance of the patient is maintained. Thus, the plasma exchange device 1118 can monitor the amount of plasma removed through outlet channels 1112 and can responsively infuse fresh or donated plasma (or other substituent) from plasma receptacle 1122 to the patient via access 1120 in proportion thereto. The removed plasma can be disposed of through waste outlet 1124.

Figure 12:
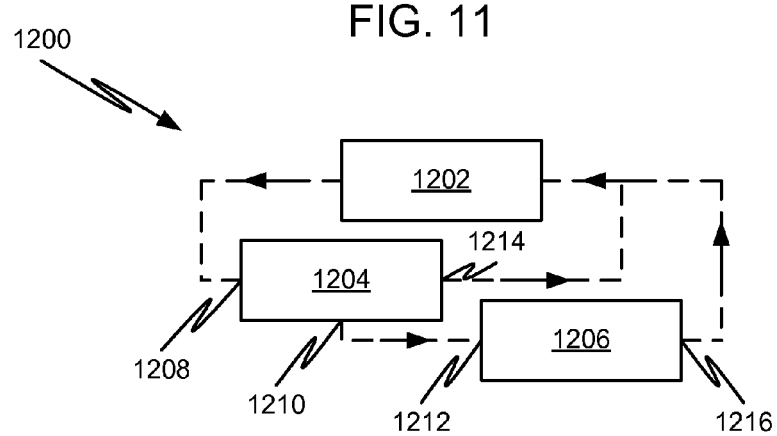
FIG. 12 is a schematic diagram of a large-scale membraneless separation device coupled to a dialyzer according to an embodiment of the disclosed subject matter.

The plasmapheresis embodiment may be extended to a embodiments in which cytoplasmic bodies are segregated in the flow in a membraneless separation device 1204 such that a cytoplasmic body-free plasma fraction can be delivered from a blood flood from a patient 1202. The resulting plasma fraction may flow from an outlet of the separation device 1204 to the input 1212 of a conventional dialyzer 1206 and/or sorbent system (not shown). Processed blood 1214 from the membraneless separation device 1204 and processed plasma 1216 from the conventional dialyzer 1206 can then be combined and returned to the patient 1202. Such a configuration 1200 is illustrated in FIG. 12.

The membraneless separation device 1204 can create separation between cytoplasmic bodies containing and CBF, in large or small volumes, without mechanical or membrane-based means so as to improve the transport efficiency of wastes from the blood. The membraneless separation device 1204 can be designed to handle large amounts of blood, for example, 200-500 ml/min. The conventional dialyzer 1206 can be enhanced and/or optimized to remove small and middle molecule solutes. As a result of this configuration 1200, smaller solutes and middle molecules, which may have been inhibited in their diffusion out of the blood, can be isolated in the extraction fluid and potentially more readily diffused into the waste. Moreover, the characteristics of the membrane of the conventional dialyzer 1206 can be enhanced and/or optimized according to a particular application or treatment modality. The conventional dialyzer 1206 can also be operated at higher shear rates than available with cytoplasmic bodies present to thereby augment the transport of all molecules without regard to the negative impact on the blood flow (thus avoiding lysis of the cells due to the higher shear rates).

In embodiment, the membraneless separation device 1204 and the conventional dialyzer 1206 are used repeatedly. In such embodiments, reusable elements sterilized, for example, using hot water sterilization at 60 to 85 degrees C. In such embodiments, the absence of cytoplasmic bodies in the dialyzer may minimize damage to hollow fibers and make sterilization techniques more effective to remove any proteins such as albumin.

Unique identification codes may be assigned to each patient and verified before each treatment session through a key kept by the patient (i.e., a USB thumb drive, or an RFID-encoded patient ID card). Through these means, the cost of conventional dialysis treatment may be reduced and patient safety thereby enhanced.

In addition to the treatment of various disease states, a device or system according to the invention can also be used for extracting blood components that are useful in treating others, as well as for purposes of studying the processes by which molecules and cytoplasmic bodies segregate and diffuse in blood. For example, diffusion of individual molecular species in blood may not occur independently and may not depend on size in the simple manner dictated by the Stokes-Einstein equation. Moreover, many solutes may partition into multiple forms: free, in complexes, bound to plasma protein, bound to cell-surface moieties, or as intracellular solutes. Relative to the rate of diffusion of the solute, its different forms may or may not be in local equilibrium. These phenomena are likely obscured when a membrane is present (and/or cytoplasmic bodies are present) because it slows and controls overall transfer rates. Therefore, a membraneless device or system according to the invention can be a useful scientific tool to study these phenomena and a system in which rates are raised enough that partitioning may set limits on how much and how quickly a solute can be removed. A particular example is bilirubin bound to albumin. Another example is inorganic phosphorous which exists as partially ionized salts, as two anionic forms in plasma and in several intracellular forms.

Figure 13A:
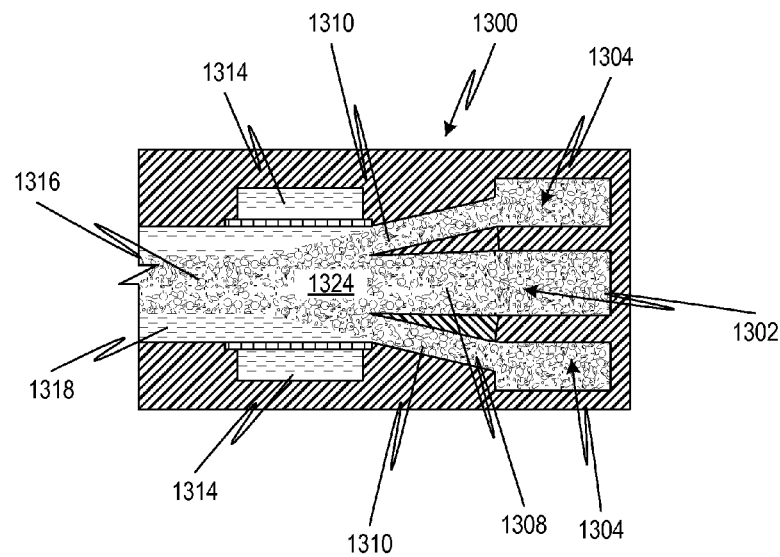
FIG. 13A is a schematic diagram of a microfluidic separator for discriminating between multiple blood components according to an embodiment of the disclosed subject matter.

Referring now to FIG. 13A, a microfluidic separator 1300 may discriminate between multiple components of blood 1316 based on the position of a respective outlet in the channel 1324. A first outlet 1308 at the center of the channel 1324 receives a stream that is rich in cells. The extraction fluid outlets 1314 receive extraction fluid 1318 and CBF. Two skimming channels 1310 adjacent the wall of the primary channel 1324 receive fluid that is enriched in smaller particles that are too big to be removed with the CBF but which may diffuse away from the channel centerline (the low shear region) such as platelets. The small particle-enriched flow is received in respective outlet plenums 1304. The cell enriched flow is received in a respective outlet plenum 1302.

Figure 13B:
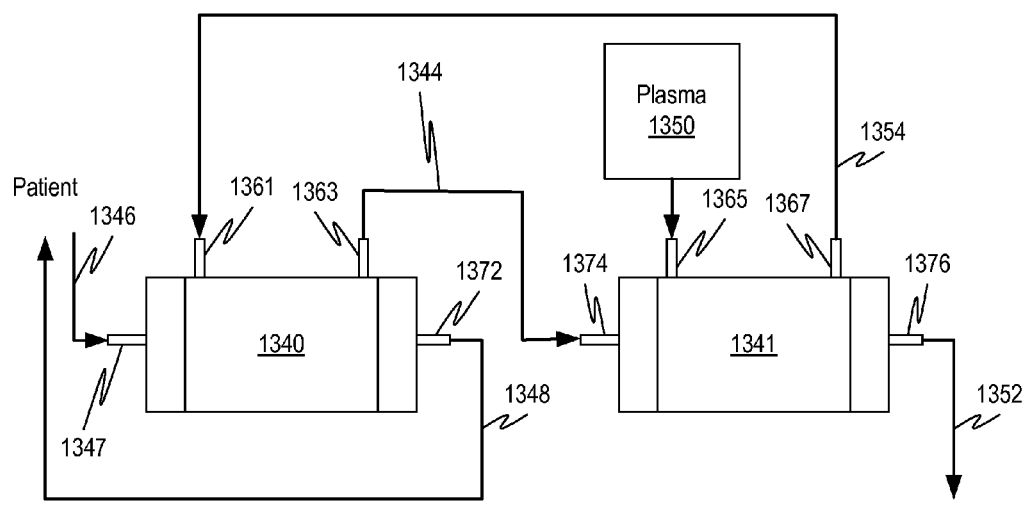
FIG. 13B is a schematic diagram of a tandem microfluidic channel device using a pair of microfluidic separators according to an embodiment of the disclosed subject matter.

Referring to FIG. 13B, a tandem microfluidic channel device has two microfluidic separators, 1340 and 1341. The first separator 1340 receives blood from a patient 1346 into its sample fluid inlet 1347 while CBF is received at the sheath fluid inlet 1361. The holes in the wall filter of the separator 1340 are sized to allow platelets to flow out of the sheath fluid outlet 1363 along with the CBF. For example, the holes may be approximately 3 µm. The cell-concentrated fraction 1348 leaves the sample fluid outlet 1372 and is returned to the patient. The platelet-containing stream 1344 enters the second separator 1341 at its sample fluid inlet 1374. The second separator 1341 wall filters (not shown here) are sized to block platelets and can have sizes in the 100 to 1000 nm range, for example. Fresh plasma enters the sheath fluid inlet 1365 and CBF 1354 leaves through the sheath fluid outlet 1367. A final product fluid 1352, which leaves the sample fluid outlet 1376, is enriched in the platelets in the platelet-containing stream and blocked by the wall filters. This product may be disposed of. A fluid balancing mechanism may be used to supply fresh plasma 1350 at the rate that product 1352 is removed.

The devices of FIGS. 13A and 13B can be used to remove middle-sized particles from any flow stream. The devices can be expanded to discriminate further sizes and can be connected in series to enhance their discriminating capability by iteratively processing and reprocessing a fluid in successive separators. An application for the devices of FIGS. 13A-13B can include removing platelets in advance of or after organ transplants to prevent complications. Another application can include removing certain types of cells from the blood which have a size feature that allows them to be discriminated.

Various embodiments described herein allow the purification of blood without the use of a membrane by contact of the blood with a miscible fluid under conditions that inhibit and/or prevent turbulent mixing. It is appreciated that embodiments described herein are useful in hemodialysis, for example. However, it should also be noted that the embodiments, and variations thereof, are also useful in other situations where exchange between a sample fluid and another fluid is desired via a diffusion mechanism.

The interface area provided by the extraction channel for a specified exchange rate can be achieved by appropriate combinations of channel length, width, and number according to the principles described herein. The required area can be obtained by providing multiple extraction channels and by providing a sheathing flow so that each channel contains two interfaces. The competing requirements of small height (to avoid excessive diffusion times and in-process volumes), short length (to avoid excessive pressure drop) and practical limitations on width of a single device suggests the need to array extraction channels in parallel, side-by-side or in a stack, all of which can be readily achieved in practical microfluidic devices.

The described embodiments can be used to process the blood of a single individual for the purpose of treating a large number of disease conditions. For example, therapies described above can be used in the treatment of acute renal failure, acute liver failure, high antibody levels in myasthenia gravis and other autoimmune diseases. Additional uses include, for example, the removal by either precipitation or sorption of LDL in homozygous hyperlipidemia, in addition to the removal of malignant sepsis or fluid in cases of congestive heart failure, for example. The described embodiments can also be used to aid in the reduction of viral burdens in AIDS patients, as well as for treatment of patients requiring other types of blood purification. Patients with diabetes, patients that have suffered a drug overdose, patients that have ingested a poison, patients suffering from renal failure, patients suffering from acute or chronic liver failure, or patients that have Myasthenia gravis, lupus erythematosis, or another autoimmune disease can also benefit from the devices and systems described above. For example, while an exchange device according to the invention is not a cure for diabetes, it can be useful in the amelioration one or more symptoms of diabetes. Moreover, the embodiment described above can be useful in clearing the blood of IgG molecules or other molecules, which are causative of an autoimmunity disorder. Additionally, embodiments according to the invention can be used in acute dialysis or for extended dialysis. Patients (or animals, in the case of veterinary use) suffering from disorders, diseases and syndromes not listed herein can also be treated.

Although the present disclosure provides several examples for blood treatment for ESRD, extraction of blood components according to the principles of the present disclosure can be used to remove other components for treatment, such as free viral particles and, in the treatment of congestive heart failure (CHF), to remove water and a non-selective cohort of electrolytes. Additional uses for extracorporeal processing include extracting blood components useful in either treating others or in research, particularly pediatric cases where conventional equipment is not available because of the substantial extracorporeal volume. Apheresis of plasma (i.e., plasmapheresis) and thrombocytes, or platelets, is the procedure most commonly employed for this purpose. Although the present specification discusses primarily blood processing and issues related thereto, many of the methods discussed may be used for processing other fluids as well, such as blood components.

Also, the extraction channel and associated elements discussed herein may be used in a secondary processor and may be chained to form multiple stages to select fluid components. For example, a chain of two extraction channels would convey the extraction fluid of a first extraction channel to the sample fluid path of a second extraction channel, thus forming a cascade. The second extractor may have, for example, filters in its walls with pore sizes that are smaller than those of the first such that the sample fluid from the second extraction channel contains intermediate sized particles, but a reduced fraction of the smallest particles. Such a cascade may include an arbitrary number of stages.

Note that in any and all embodiments, the membraneless channels may employ channel filters such as indicated at 330 in FIG. 4 and similar filters discussed herein and in U.S. Patent Application Publication No. 2006/0076295 incorporated herein.

Methods, systems, and devices for fluid separation are described herein. In particular, the described methods, system, and devices can employ a membraneless separation device as the first stage for processing biological fluids, such as, but not limited to, blood from a patient. The membraneless separation device can perform plasmapheresis in a continual, non-mechanical fashion, with or without the use of anti-coagulants, thereby producing a platelet-free and cytoplasmic body-free plasma stream from which solutes and/or fluid can be extracted, also with or without the use of anti-coagulants, in a later stage using traditional or other means. The membraneless separation device can be applied to a variety of treatments, such as the treatment of blood for a patient with ESRD or CHF. For example, the blood of the patient can undergo ultrafiltration using a membraneless separation device to remove excess fluid from the patient.

A device for performing ultrafiltration can include (i.e., comprise) a first stage that separates an incoming blood flow into a substantially cytoplasmic body-free plasma flow and a fraction enriched in cytoplasmic bodies. The device can also have (i.e., comprise) a dialysate-free second stage, which receives the substantially cytoplasmic body-free plasma flow from the first stage. The second stage can selectively remove excess fluid, toxins and other substances from the plasma flow and return the processed plasma to an inlet of the first stage. A housing can contain both the first and second stages.

A method for removing excess fluid from a patient can include removing blood from the patient, separating from a remainder of the blood a plasma fraction, i.e., a blood fraction that is substantially free of cytoplasmic bodies, including cells (erythrocytes and leukocytes) and platelets. The method continues with ultrafiltering the CBF by using a membrane in the absence of a medicament such as dialysate, for example, by flowing the plasma fraction past a membrane, such as a plurality of hollow fiber membranes in an extracorporeal.

A method for treating a patient can include flowing the patient's blood in non-mixing direct contact with an extraction fluid, which includes medicament, such as dialysate, thereby transferring a CBF to the extraction fluid. The extraction fluid may include, in addition to medicament, a portion of CBF previously separated from the blood and circulated back into contact with the patient's blood (a recirculated flow). The non-mixing contact may be a concurrent flow in a flat separation channel. The extraction fluid and patient's blood flowing in the separation channel are maintained such that there is substantially no stress and strain at the interface of the blood and extraction fluid. Thus, no advection or non-diffusive mixing is present. The extraction fluid can be separated from a remainder of the flowing blood by drawing the extraction fluid from the separation channel at an outlet thereof. The extraction fluid may include CBF or a modified CBF (resulting from a conditioning in the recirculated flow, such as ultrafiltration or exposure to a sorbent or chemical agent) in combination with fresh or recycled and/or regenerated medicament. A treatment may be performed on the recirculated flow with CBF, including ultrafiltration, photopheresis, sorbent-based renal toxin removal, or other treatment.

Another method for treating a patient can include spatially separating a first component from a second component of a biological fluid containing cytoplasmic bodies using a laminar flow of the biological fluid in a microchannel, and supplying the separated first component to a treatment system. In a variation, the spatial separation is performed in a flat microchannel under conditions that cause cytoplasmic bodies in the biological fluid to concentrate in one layer of the laminar flow, allowing a CBF to be isolated. The CBF may be in the form of a layer which may be extracted from the microchannel. The extracted CBF may be subjected to a treatment in a recirculated flow. The extracted CBF and patient's blood flowing in the flat microchannel are maintained such that there is substantially no stress and strain at the interface of the blood and extraction fluid.

A method for treating a patient can include flowing a patient's blood in non-mixing direct contact with an extraction fluid. The extraction fluid may include a recirculated fluid that includes CBF previously extracted from the blood and subject to a treatment before placing back into contact with the blood. The non-mixing contact may be a concurrent flow in a flat separation channel. The extraction fluid and patient's blood flowing in the separation channel are maintained such that there is substantially no stress and strain at the interface of the blood and extraction fluid. The extraction fluid can be separated from a remainder of the flowing blood by drawing the extraction fluid from the separation channel at an outlet thereof. The extraction fluid may include CBF or a CBF modified as a result of being conditioned in the recirculated flow by, for example, ultrafiltration, exposure to a sorbent or chemical agent, or dilution, or dialytic regeneration. A treatment may be performed on the recirculated flow with CBF, including ultrafiltration, photopheresis, sorbent-based renal toxin removal, or other treatment.

A treatment protocol for treating a patient with chronic renal disease can include ultrafiltering blood of a patient using an ambulatory or portable ultrafiltration device, which ultrafilters the blood without connection to a substantial supply of medicament including replacement fluid, dialysate, or any other consumable exogenous fluid. The ultrafiltering can be performed for a first treatment time and can be repeated at a first frequency. A secondary treatment can also be performed on the blood of a patient. However, the secondary treatment is performed for a second treatment time and can be repeated at a second frequency less than the first frequency. In a particular embodiment, the ultrafiltering is done using a membraneless separation device, system, or method.

In a further more particular embodiment, the ultrafiltration employing the membraneless separation device includes the separation of fluid and uremic toxins from the blood and may include various combination of components (or phases), which may occur concurrently or sequentially. These include:
- a first component in which the fluid and uremic toxins are captured in a co-flowing extraction fluid (which may include an exogenous fluid or consist primarily or entirely of recycled CBF), primarily through advective diffusion, while cytoplasmic bodies move to, or are retained in, a relatively low shear layer of the flow;
- a second component in which the extraction fluid, including water, uremic toxins, and other blood components, but not cytoplasmic bodies, are removed from a relatively high shear layer of the flow in the membraneless channel;
- a third component that includes filtering of the flow of fluid from the membraneless channel through a nanoporous filter which ensures the cytoplasmic bodies are not extracted from the extraction fluid flow; and
- a fourth component in which water and relatively small molecules, including uremic toxins, are removed by them through a membrane and the remaining fluid recycled to the membraneless separation channel.

The membraneless separation device can also be applied to analysis, collection and/or exchange of plasma from blood. For example, a method for blood analysis can include providing an input blood flow from a patient to a membraneless separation device, flowing the blood flow through the membraneless separation device such that a CBF is spatially separated from a remaining fraction of the blood, flowing the CBF through an outlet and analyzing the cytoplasmic body-free plasma fraction from the outlet. A device for analyzing blood plasma can include a membraneless separator having a blood inlet and a plasma outlet. The membraneless separator can be configured to generate a plasma flow at the plasma outlet from a blood flow at the blood inlet. The device can also include at least one of an analyzer and a sample reservoir connected to the plasma outlet. The extraction of plasma employing the membraneless separation device includes the separation of CBF from the blood and may include various combination of components (or phases), which may occur concurrently or sequentially. These include:

a first component in which the plasma fluid are separated from cytoplasmic bodies by a formation of layers in which the cytoplasmic bodies are moved toward, or retained in, a low shear layer of the flow and the cytoplasmic body-free (or depleted) plasma is segregated to a relatively high shear layer;

a second component in which the plasma is removed from the relatively high shear layer of the flow in the membraneless channel;

a third component that includes filtering of the flow of fluid from the membraneless channel through a nanoporous filter which ensures the cytoplasmic bodies are not extracted from the extraction fluid flow; and a fourth component in which the plasma is discarded or provided to an analyzer or sample reservoir. The latter may be attended by a replacement of extracted plasma from a source of fresh plasma in plasma exchange therapy embodiments.

A method for exchanging plasma of a patient can include flowing blood from a patient through a membraneless separation device such that a CBF is spatially separated from a remainder of the blood, extracting the CBF, and providing to the patient an amount of substitute fluid at substantially a same rate as the extraction of the separated plasma. In an embodiment, the CBF extracted and the substitute flows are substantially plasma.

A device for plasma exchange can include a membraneless separation device configured to extract at least a plasma component from the blood of a patient, and a flow regulator configured to meter a substitute fluid, for example, fresh plasma for infusion into the patient at substantially a same rate as a rate of extraction of the plasma component by the membraneless separation device.

Although particular configurations have been discussed herein, other configurations can also be employed. Furthermore, the foregoing descriptions apply, in some cases, to examples generated in a laboratory, but these examples can be extended to production techniques. For example, where quantities and techniques apply to the laboratory examples, they should not be understood as limiting.

It is, thus, apparent that there is provided, in accordance with the present disclosure, systems, methods and devices for processing biological fluids using a membraneless separation device. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method for treating chronic renal disease of a patient comprising:
    (a) for a duration of at least 4 hours, performing an ultrafiltration process by using a portable treatment device having a membraneless microfluidic channel, said performing including:
        (a1) passing blood at a flow rate into the membraneless microfluidic channel having dimensions such that, at the blood flow rate, a fraction depleted of cytoplasmic bodies from the blood is generated;
        (a2) removing a portion of the fraction depleted of cytoplasmic bodies from the membraneless microfluidic channel;
        (a3) extracting at least water from the removed portion of the fraction depleted of cytoplasmic bodies using a first membrane; and
        (a4) returning the removed portion of the fraction depleted of cytoplasmic bodies, minus some water, back to the patient;
        an ultrafiltration rate of the ultrafiltration process resulting in a rate of production of ultrafiltrate of less than 0.4 l/hr;
    (b) repeating the performing an ultrafiltration process at least daily, the ultrafiltration process requiring no continuous consumption of exogenous fluid; and
    (c) at a frequency that is less than daily, using another treatment device to perform a renal replacement therapy in which blood components are exchanged between blood and a sorbent or between blood and a substantial supply of exogenous fluid across a second membrane, the blood contacting the second membrane or the sorbent of the another treatment device;
    the repeating either being done on days in which the performing a renal replacement therapy is done or being skipped on the days in which the performing a renal replacement therapy is done.

2. The method of claim 1, wherein the removing a portion of the fraction depleted of cytoplasmic bodies includes blocking the exit of cytoplasmic bodies from the membraneless microfluidic channel by passing the fraction depleted of cytoplasmic bodies through a wall filter having an array of holes whose sizes are less than 1000 nm, the wall filter forming a part of a wall of the membraneless microfluidic channel.

3. The method of claim 1, wherein the removing a portion of the fraction depleted of cytoplasmic bodies includes blocking the exit of cytoplasmic bodies from the membraneless microfluidic channel by passing the fraction depleted of cytoplasmic bodies through a wall filter having an array of holes whose sizes are between 600 and 1000 nm, the wall filter forming a part of a wall of the membraneless microfluidic channel and forming a continuous unobstructed and smooth surface with the wall of the membraneless microfluidic channel.

4. The method of claim 1, wherein the blood flow rate is at least 0.5 ml/second and less than 5 ml/sec.

5. The method of claim 1, wherein the ultrafiltration process includes positioning the portable device, including the membraneless microfluidic channel, proximate the patient such that blood volume outside the patient's body is minimized by minimizing a volume of blood channels.

6. The method of claim 1, wherein the renal replacement therapy includes at least one of hemofiltration, hemodialysis, and hemodiafiltration.

7. The method of claim 1, wherein the renal replacement therapy includes sorption-based dialysis.

8. The method of claim 1, wherein the renal replacement therapy includes dialysis in which blood and a supply of dialysate of at least 10 L are passed across opposite sides of a membrane at least to clear uremic toxins from the blood.

9. The method of claim 1, wherein the ultrafiltration process includes passing the fraction depleted of cytoplasmic bodies across a sorbent configured to remove at least urea therefrom.

10. The method of claim 1, further comprising, prior to the performing an ultrafiltration process, priming the membraneless microfluidic channel and wetting the first membrane of the portable treatment device.

11. The method of claim 1, wherein:
the portable treatment device comprises a detector that monitors the blood flow or the removed portion of the fraction depleted of cytoplasmic bodies; and
said performing an ultrafiltration process is performed responsively to a signal from said detector.

12. The method of claim 1, further comprising, periodically reversing flow through the wall filter in the membraneless microfluidic channel so as to flush a surface of the wall filter.

13. The method of claim 1, wherein the portable treatment device comprises a waste receptacle that receives the at least water extracted from the removed portion of the fraction depleted of cytoplasmic bodies.

14. The method of claim 1, wherein the portable treatment device is configured to perform a treatment without use of exogenous fluids, and the another treatment device is a non-portable device configured to perform a treatment using exogenous fluids.

* * * * *